US012310947B2

(12) United States Patent
Philpot et al.

(10) Patent No.: US 12,310,947 B2
(45) Date of Patent: May 27, 2025

(54) METHODS AND COMPOSITIONS FOR UNSILENCING IMPRINTED GENES

(71) Applicant: The University of North Carolina at Chapel Hill, Chapel Hill, NC (US)

(72) Inventors: Benjamin D. Philpot, Durham, NC (US); Kiran Ramesh Bettadapur, Bengaluru (IN); Hyeong-Min Lee, Cordova, TN (US); Hanna Vihma, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 813 days.

(21) Appl. No.: 17/625,604

(22) PCT Filed: Jul. 16, 2020

(86) PCT No.: PCT/US2020/042379
§ 371 (c)(1),
(2) Date: Jan. 7, 2022

(87) PCT Pub. No.: WO2021/011802
PCT Pub. Date: Jan. 21, 2021

(65) Prior Publication Data
US 2022/0265607 A1    Aug. 25, 2022

Related U.S. Application Data

(60) Provisional application No. 62/874,777, filed on Jul. 16, 2019.

(51) Int. Cl.
*A61K 31/4155*  (2006.01)
*A61K 31/166*   (2006.01)
*A61K 31/42*    (2006.01)
*A61P 25/00*    (2006.01)

(52) U.S. Cl.
CPC ........ *A61K 31/4155* (2013.01); *A61K 31/166* (2013.01); *A61K 31/42* (2013.01); *A61P 25/00* (2018.01)

(58) Field of Classification Search
CPC .................................................. A61K 31/4155
See application file for complete search history.

(56) References Cited

U.S. PATENT DOCUMENTS

| 9,714,427 B2 | 7/2017 | Philpot et al. |
| 10,301,630 B2 | 5/2019 | Philpot et al. |
| 2018/0016584 A1 | 1/2018 | Philpot et al. |

FOREIGN PATENT DOCUMENTS

WO    2014004572 A2    1/2014

OTHER PUBLICATIONS

Bovio et al. "Differential Methylation of H3K79 Reveals DOT1L Target Genes and Function in the Cerebellum In Vivo" Molecular Neurobiology, 56:4273-4287 (2019).
International Search Report and the Written Opinion of the International Searching Authority corresponding to International Patent Application No. PCT/US2020/042379 (12 pages) (mailed Nov. 6, 2020).
Kaniskan et al. "Inhibitors of Protein Methyltransferases and Demethylases" Chemical Reviews, 118:989-1068 (2018).
Mirabella et al. "Chromatin deregulation in disease" Chromosoma, 125:75-93 (2016).
Daigle et al. "Potent inhibition of DOT1L as treatment of MLL-fusion leukemia" Blood, 122(6):1017-1025 (2013).
Huang et al. "Topoisomerase inhibitors unsilence the dormant allele of Ube3a in neurons" Nature, 481(7380):185-189 (2011).
International Preliminary Report on Patentability corresponding to International Patent Application No. PCT/US2020/042379 (7 pages) (dated Jan. 27, 2022).
Judson et al. "Allelic Specificity of Ube3a Expression in the Mouse Brain during Postnatal Development" The Journal of Comparative Neurology, 522(8):1874-1896 (2014).
Pevarello et al. "3-Aminopyrazole Inhibitors of CDK2/Cyclin A as Antitumor Agents. 2. Lead Optimization" Journal of Medicinal Chemistry, 48(8):2944-2956 (2005).

*Primary Examiner* — Yong S. Chong
(74) *Attorney, Agent, or Firm* — Myers Bigel, P.A.

(57) ABSTRACT

The present invention provides methods and compositions for inducing expression of Ube3a in a cell and treating Angelman syndrome in a subject.

5 Claims, 24 Drawing Sheets
Specification includes a Sequence Listing.

PHA533533

P5-A1

P5-A2

P5-A3

P5-A4

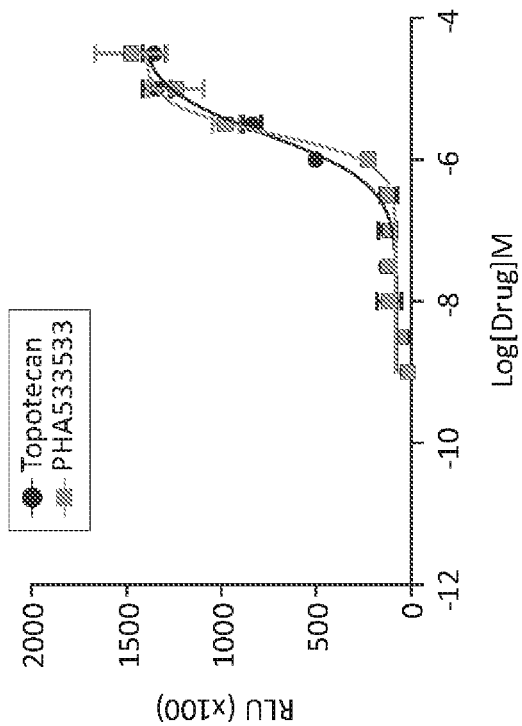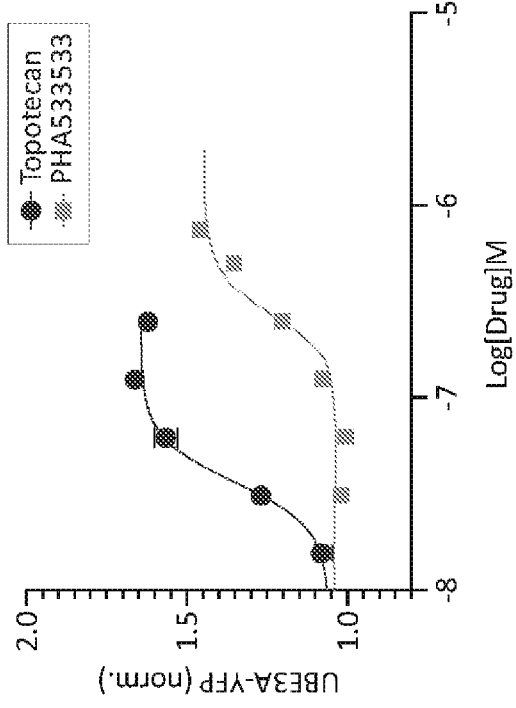
FIG. 9A  FIG. 9B  FIG. 9C  FIG. 9D  FIG. 9E

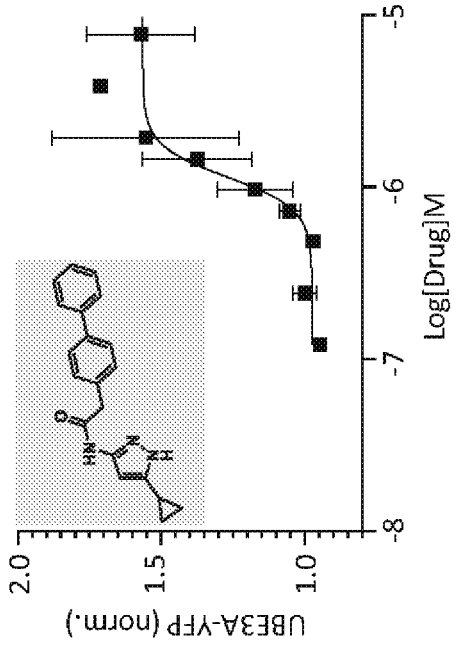
FIG. 10A
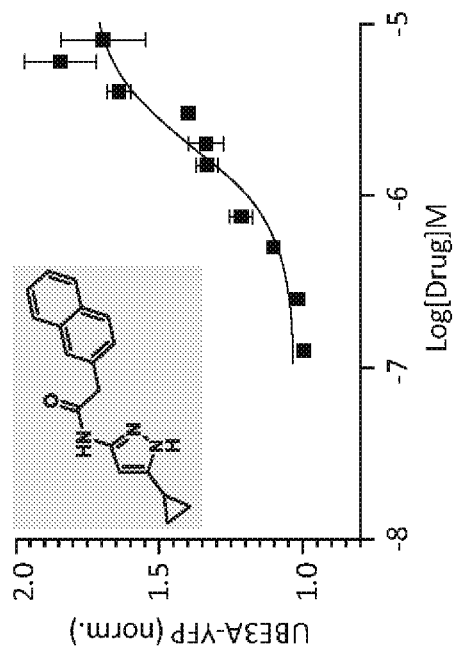
FIG. 10B
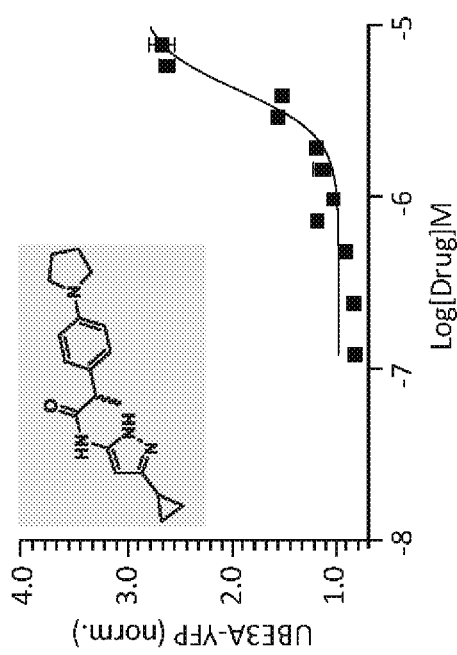
FIG. 10C
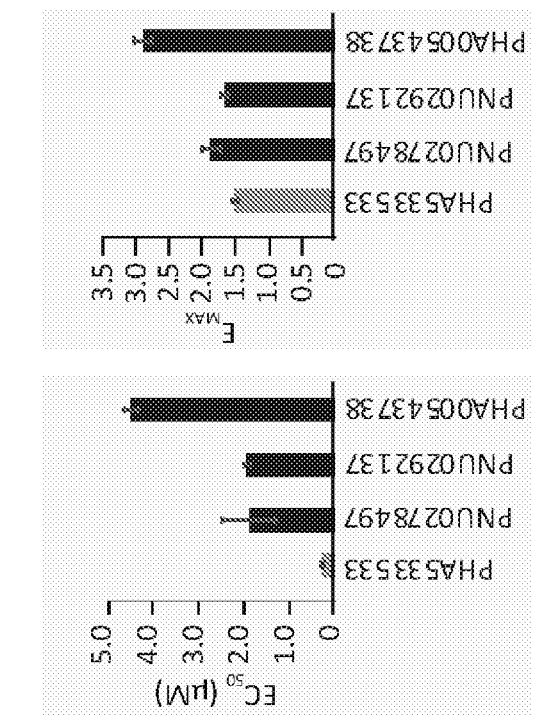
FIG. 10D
FIG. 10E

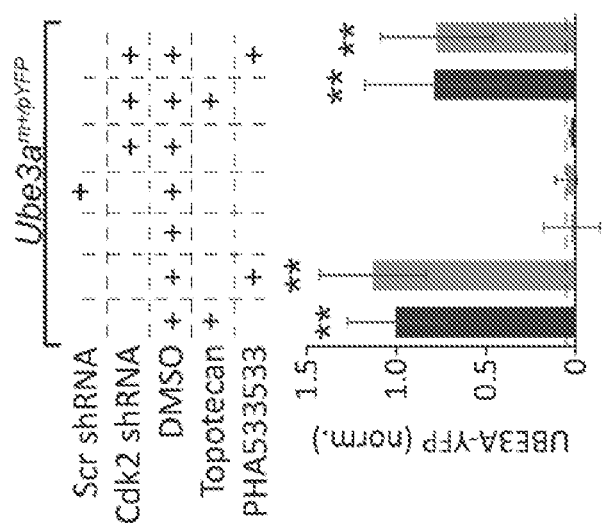
FIG. 13C
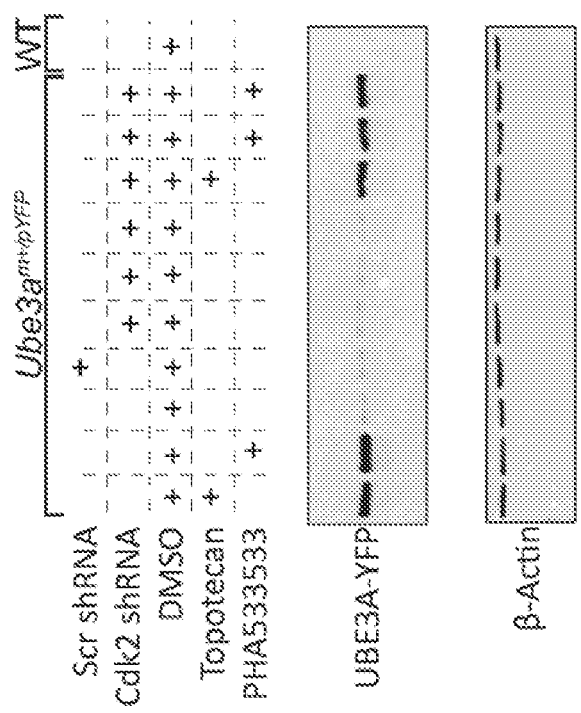
FIG. 13A  FIG. 13B
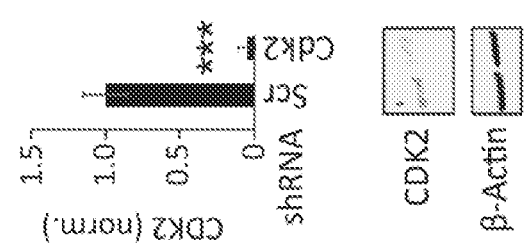

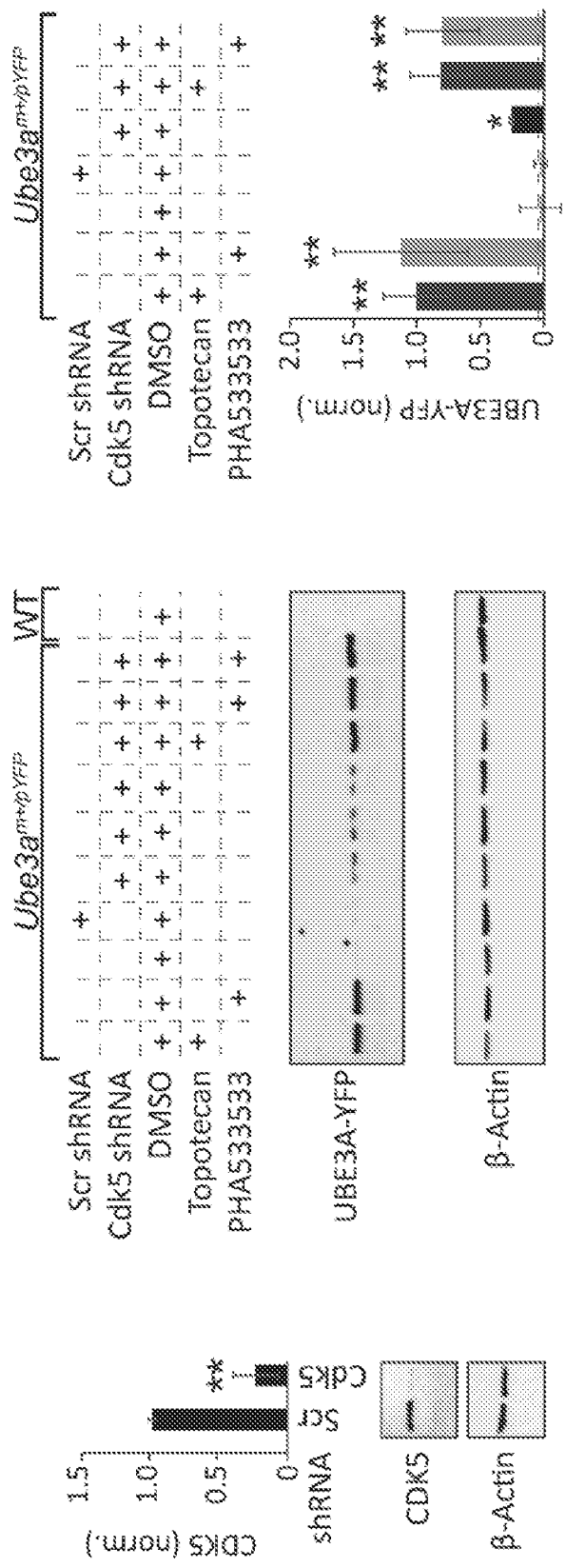

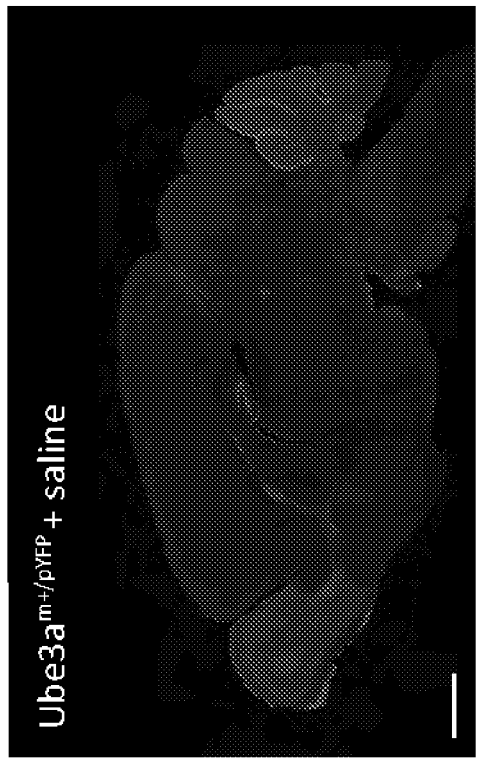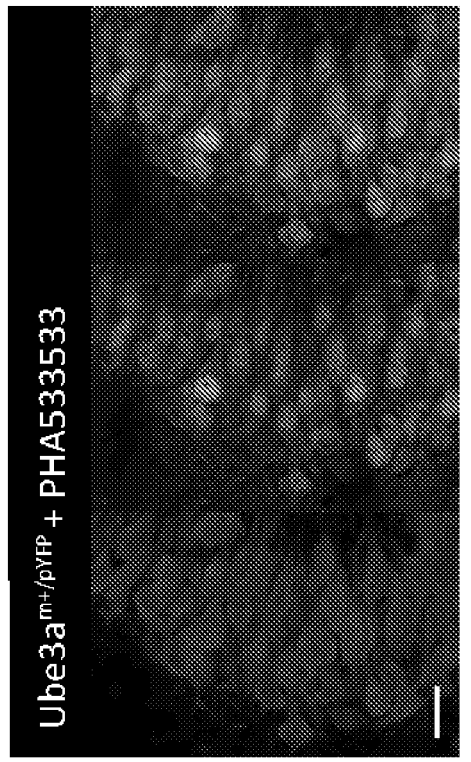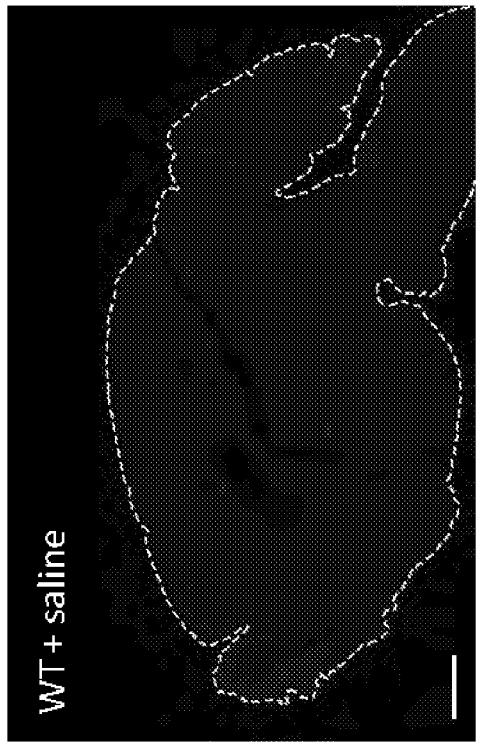

SEQUENCE LISTING

<160> NUMBER OF SEQ ID NOS: 10

<210> SEQ ID NO 1
<211> LENGTH: 20
<212> TYPE: DNA
<213> ORGANISM: Artificial

```
<220> FEATURE:
<223> OTHER INFORMATION: beta-actin forward primer

<400> SEQUENCE: 1
agagctacga gctgcctgac                                               20

<210> SEQ ID NO 2
<211> LENGTH: 20
<212> TYPE: DNA
<213> ORGANISM: Artificial
<220> FEATURE:
<223> OTHER INFORMATION: beta-actin reverse primer

<400> SEQUENCE: 2
agcactgtgt tggcgtacag                                               20

<210> SEQ ID NO 3
<211> LENGTH: 21
<212> TYPE: DNA
<213> ORGANISM: Artificial
<220> FEATURE:
<223> OTHER INFORMATION: YFP forward primer

<400> SEQUENCE: 3
acatgaagca gcacgacttc t                                             21

<210> SEQ ID NO 4
<211> LENGTH: 24
<212> TYPE: DNA
<213> ORGANISM: Artificial
<220> FEATURE:
<223> OTHER INFORMATION: YFP reverse primer

<400> SEQUENCE: 4
gacgttgtgg ctgttgtagt tgta                                          24

<210> SEQ ID NO 5
<211> LENGTH: 23
<212> TYPE: DNA
<213> ORGANISM: Artificial
<220> FEATURE:
<223> OTHER INFORMATION: Ube3a-ATS forward primer

<400> SEQUENCE: 5
acagaacaat aggtcaccag gtt                                           23

<210> SEQ ID NO 6
<211> LENGTH: 21
<212> TYPE: DNA
<213> ORGANISM: Artificial
<220> FEATURE:
<223> OTHER INFORMATION: Ube3a-ATS reverse primer

<400> SEQUENCE: 6
aagcaagact gttcacctca t                                             21

<210> SEQ ID NO 7
<211> LENGTH: 22
<212> TYPE: DNA
<213> ORGANISM: Artificial
<220> FEATURE:
<223> OTHER INFORMATION: Snrpn forward primer

<400> SEQUENCE: 7
ttggttctga ggagtgattt gc                                            22
```

```
<210> SEQ ID NO 8
<211> LENGTH: 20
<212> TYPE: DNA
<213> ORGANISM: Artificial
<220> FEATURE:
<223> OTHER INFORMATION: Snrpn reverse primer

<400> SEQUENCE: 8
ccttgaattc caccaccttg                                               20

<210> SEQ ID NO 9
<211> LENGTH: 20
<212> TYPE: DNA
<213> ORGANISM: Artificial
<220> FEATURE:
<223> OTHER INFORMATION: Snord116 forward primer

<400> SEQUENCE: 9
ggatctatga tgattcccag                                               20

<210> SEQ ID NO 10
<211> LENGTH: 18
<212> TYPE: DNA
<213> ORGANISM: Artificial
<220> FEATURE:
<223> OTHER INFORMATION: Snord116 reverse primer

<400> SEQUENCE: 10
ggacctcagt tccgatga                                                 18
```

US 12,310,947 B2

METHODS AND COMPOSITIONS FOR UNSILENCING IMPRINTED GENES

STATEMENT OF PRIORITY

This patent application is a 35 U.S.C. § 371 national phase application of PCT Application PCT/US2020/042379 filed Jul. 16, 2020, which claims the benefit, under 35 U.S.C. § 119 (e), of U.S. Provisional Application No. 62/874,777, filed on Jul. 16, 2019, the entire contents of each of which are incorporated by reference herein.

STATEMENT OF GOVERNMENT SUPPORT

This invention was made with government support under Grant Number HD040127 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-866 ST25.txt, 2.277 bytes in size, generated on Jan. 5, 2022 and filed via EFS-Web, is provided in lieu of a paper copy. This Sequence Listing is hereby incorporated herein by reference into the specification for its disclosures.

FIELD OF THE INVENTION

The present invention is directed to methods and compositions for inducing expression of Ube3a in a cell and treating Angelman syndrome in a subject.

BACKGROUND OF THE INVENTION

Angelman syndrome (AS) is a neurodevelopmental disorder affecting ~1:20,000 individuals and characterized by developmental delay, intellectual disability, speech impairment, seizures, and ataxia. No effective therapies currently exist, however the unique epigenetics of AS offer a potential therapeutic avenue. AS is caused by mutations of the ubiquitin protein ligase E3A (UBE3A) gene, which exhibits parent-of-origin genomic imprinting. Only the maternal-inherited copy of UBE3A is expressed in neurons, while the paternal-inherited copy is intact but silent. On the other hand, UBE3A is biallelically expressed in non-neuronal cells. Although the detailed mechanism of this genomic imprinting remains unclear, an imprinting center regulates DNA methylation and gene expression in cis. Expression of the paternal UBE3A allele is competitively restricted in neurons by expression of UBE3A antisense transcript (UBE3A-ATS), which is not fully expressed in non-neuronal cells due to the presence of a bipartite boundary element.

The present invention provides methods and compositions for unsilencing imprinted genes (e.g., the paternal allele of Ube3a silenced through epigenetic imprinting), thereby providing methods of treatment of genomic imprinting disorders, such as Angelman syndrome.

SUMMARY OF THE INVENTION

In one aspect, the present invention provides a method of inducing expression of Ube3a in a cell, comprising contacting the cell with an effective amount of one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3, thereby inducing expression of Ube3a in the cell.

An additional aspect of the present invention is a method of treating Angelman Syndrome in a human subject, comprising administering to the subject an effective amount of one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3, thereby treating Angelman syndrome in the subject.

A further aspect of this invention includes a method of treating a disorder associated with an epigenetic modification in a subject, comprising administering to the subject an effective amount of an inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3, thereby treating the disorder associated with the epigenetic modification in the subject.

An additional aspect of the present invention is a method of inducing expression of Ube3a in a cell, comprising contacting the cell with an effective amount of PHA533533 or a salt thereof, (R)—N-(5-cyclopropyl-1H-pyrazol-3-yl)-2-(4-(2-oxopyrrolidin-1-yl)phenyl)propenamide, (S)—N-(5-cyclopropyl-1H-pyrazol-3-yl)-2-(4-(2-oxooxazolidin-3-yl)phenyl)propenamide, and/or EPZ5676 in any combination, thereby inducing expression of Ube3a in the cell.

Another aspect of the present invention is a method of treating Angelman Syndrome in a human subject, comprising administering to the subject an effective amount of PHA533533 or a salt thereof, (R)—N-(5-cyclopropyl-1H-pyrazol-3-yl)-2-(4-(2-oxopyrrolidin-1-yl)phenyl)propenamide, (S)—N-(5-cyclopropyl-1H-pyrazol-3-yl)-2-(4-(2-oxooxazolidin-3-yl)phenyl)propenamide, and/or EPZ5676 in any combination, thereby treating Angelman syndrome in the subject.

Another aspect of the present invention is the use of PHA533533 or a salt thereof, (R)—N-(5-cyclopropyl-1H-pyrazol-3-yl)-2-(4-(2-oxopyrrolidin-1-yl)phenyl)propenamide, (S)—N-(5-cyclopropyl-1H-pyrazol-3-yl)-2-(4-(2-oxooxazolidin-3-yl)phenyl)propenamide, and/or EPZ5676 in any combination in the manufacture of a medicament for the treatment of Angelman Syndrome.

A further aspect of the present invention is the use of PHA533533 or a salt thereof, (R)—N-(5-cyclopropyl-1H-pyrazol-3-yl)-2-(4-(2-oxopyrrolidin-1-yl)phenyl)propenamide, (S)—N-(5-cyclopropyl-1H-pyrazol-3-yl)-2-(4-(2-oxooxazolidin-3-yl)phenyl)propenamide, and/or EPZ5676 in any combination in the manufacture of a medicament for inducing expression of Ube3a in a cell.

DESCRIPTION OF THE FIGURES

FIG. 1A shows the chemical structures of topotecan and PHA533533. FIG. 1B shows immunofluorescent images of nuclei (Hoechst stain) or paternal UBE3A-YFP (GFP-antibody enhanced) in cultured mouse cortical neurons. Paternal Ube3a-YFP was unsilenced by PHA533533 and Compound X, but not by 0.1% DMSO vehicle control (scale bar=100 μm). Topotecan served as a positive control for unsilencing. FIG. 1C shows quantitative analysis of UBE3A-YFP. The percentage of neurons expressing paternal UBE3A-YFP was calculated by dividing the number of YFP-positive cells by the total number of nuclei (n=4/group, p<0.01, *p<0.001). FIG. 1D shows results from a compound screening of the Pfizer chemogenetic library for paternal Ube3a unsilencing agents. Data were normalized to fluorescent intensity and shown as means±s.e.m. (n=4/compound). A reliable increase to >1.25 of normalized fluorescent intensity (red line) served as an arbitrary cutoff for hit identification.

FIG. 2A shows dose-dependence of two novel unsilencers compared to topotecan in unsilencing paternal Ube3a-YFP (n=4/group). Fluorescent intensity of paternal UBE3A-YFP was normalized to vehicle control. FIG. 2B shows dose-dependent cytotoxicity of two novel unsilencers compared to topotecan (n=4/group). Luminescence produced by dead-cell protease activity was measured using the Cyto Tox-Glo assay (Promega). FIG. 2C shows $EC_{50}$, FIG. 2D shows $E_{max}$, and FIG. 2E shows $LC_{50}$ of the compounds were estimated (n=4/group, two-way ANOVA with Bonferroni correction for multiple comparison, **p<0.01).

FIGS. 3A and 3B show Western blot analyses that, like topotecan, PHA533533 and Compound X can produce UBE3A-YFP (FIG. 3A) and UBE3A (FIG. 3B) protein from the paternal allele, while control Compound Y has no effect. Whole cell lysates from cultured mouse cortical neurons (wildtype, Ube3a$^{m+/pYFP}$, or Ube3a$^{m-/p+}$ as indicated) were resolved using SDS-PAGE and immunoblotted with (FIG. 3A) anti-GFP, (FIG. 3B) anti-Ube3a, or (FIGS. 3A-3B) anti-β-actin. Graphs show quantification of normalized signal. DMSO=0.1% vehicle control; Topotecan=0.3 µM; PHA533533=1.0 µM; Compound X=0.5 µM; control Compound Y=0.5 µM (n=3/group, *p<0.05, p<0.01, *p<0.001). FIGS. 3C-3F show quantitative RT-PCR (qPCR) revealed changes in mRNA of (FIG. 3C) Ube3a-YFP, (FIG. 3D) Ube3a-antisense (ATS), (FIG. 3E) Snord116, and (FIG. 3F) Snrpn in cultured mouse cortical neurons after drug treatment. Graphs represent relative mRNA levels normalized to β-actin and shown as means±s.e.m. (RQ: Relative quantity, n=3/group, *p<0.05, p<0.01, *p<0.001). FIG. 3G shows the chemical structures of PHA533533 and four analogues thereof.

FIG. 4A shows efficient knockdown of cyclin-dependent kinase 2 (CDK2) did not unsilence paternal Ube3a-YFP unless neurons were treated with topotecan or PHA533533. FIG. 4B shows efficient knockdown of CDK5 partially unsilenced paternal Ube3a-YFP, but unsilencing was further enhanced by treatment of topotecan or PHA533533. FIG. 4C shows knockdown of topoisomerase 1 (Top 1) did not unsilence paternal Ube3a-YFP unless neurons were treated with PHA533533. Whole cell lysates were resolved using SDS-PAGE and immunoblotted with anti-GFP and anti-β-actin. For FIGS. 4A-4C each: Left: Knockdown of CDK2, CDK5, and Top1 (n=3/group, p<0.01, *p<0.001). Middle: Immunoblot with anti-GFP and anti-β-actin. Right: Quantitative analysis of UBE3A-YFP unsilencing normalized to β-actin. scr: scrambled shRNA control, WT: wildtype; DMSO, (0.1% vehicle control); Topotecan (0.3 µM), PHA533533 (1.0 µM) (n=3/group, *p<0.05, **p<0.01).

FIG. 5A shows topoisomerase-based DNA relaxation assay showing that PHA533533 and Compound X partially inhibits Top2a whereas control Compound Y completely inhibits Top2a. ICRF-193, a known Top2a and 2b inhibitor, serves as a positive control. FIG. 5B shows Western blot analysis suggesting that dual inhibition of CDK5 and DOT1L is sufficient for unsilencing of paternal Ube3a-YFP. Whole cell lysates from cultured mouse cortical neurons (Ube3a$^{m+/pYFP}$) after drug treatment were resolved using SDS-PAGE and immunoblotted with anti-GFP, anti-H3K79me (di- and tri-), or anti-β-actin. Left: immunoblot with anti-GFP, anti-H3K79me2, anti-H3K79me3, and anti-β-actin. Right: quantitative analysis of H3K79me and unsilenced Ube3a-YFP. Levels were normalized to β-actin. WT: wildtype, DMSO (0.1% vehicle control); Topotecan (0.3 µM); PHA533533 (1.0 µM); Compound X (0.5 µM); and control Compound Y (0.5 µM); EPZ5676 (3 µM); and EPZ5676 (1 µM) with P5-A4 (1 µM) (n=3/group, *p<0.05, p<0.01, *p<0.001). FIGS. 5C-5F show quantitative RT-PCR showing changes in the mRNA levels of (FIG. 5C) Ube3a-YFP, (FIG. 5D) Ube3a-ATS, (FIG. 5E) Snord116, and (FIG. 5F) Snrpn in cultured mouse cortical neurons after drug treatment. Expression was normalized relative to β-actin and shown as means±s.e.m. (RQ: Relative quantity, n=3/groups, *p<0.05, **p<0.01).

FIG. 8A shows a schematic of the high content imaging screen. Paternal UBE3A-YFP levels were assessed using GFP antibody-enhanced fluorescence and high-content imaging. FIG. 8B shows DAPI (nuclear stain) and paternal UBE3A-YFP immunocytochemistry in cultured neurons treated with 0.1% DMSO (negative control), topotecan (positive control), S-enantiomer of PHA533533, R-enantiomer of PHA533533, or a racemic mixture of S and R enantiomers of PHA533533. FIG. 8C shows quantitative analysis of the percentage of cells expressing paternal UBE3A-YFP, calculated by dividing the number of YFP-positive cells by the total number of DAPI-positive nuclei (n=4/group, p<0.01, *p<0.001).

FIGS. 9A-9E show pharmacological profile of PHA533533 in unsilencing paternal Ube3a-YFP in vitro. FIG. 9A shows dose-dependence of PHA533533 compared to topotecan in unsilencing paternal Ube3a-YFP (n=4/group). Fluorescent intensity of paternal UBE3A-YFP was normalized to vehicle control. FIG. 9B shows dose-dependent cytotoxicity of PHA533533 compared to topotecan (n=4/group). Luminescence produced by dead-cell protease activity was measured using the Cyto Tox-Glo assay (Promega). FIG. 9C shows $EC_{50}$, FIG. 9D shows $E_{max}$, and FIG. 9E shows $LC_{50}$ of the compounds shown as mean s.e.m.

FIGS. 10A-10E show pharmacological profile of PHA533533 analogs in unsilencing paternal Ube3a-YFP in vitro. FIGS. 10A-10C show dose-dependence of PHA533533 analogs (FIG. 10A) PNU0292137, (FIG. 10B) PNU0278497, and (FIG. 10C) PHA00543738 in unsilencing paternal Ube3a-YFP (n=4/group). Fluorescent intensity of paternal UBE3A-YFP was normalized to vehicle control. FIG. 10D shows $EC_{50}$ and FIG. 10E shows $E_{max}$ of the PHA533533 and its analogs shown as mean±s.e.m.

FIGS. 13A-13I show that selective knockdown of established PHA533533 molecular targets is not sufficient to unsilence paternal Ube3a-YFP as effectively as PHA533533. FIG. 13A shows knockdown of cyclin-dependent kinase 2 (CDK2). FIG. 13B shows Western blot analysis and FIG. 13C shows quantification of shRNA knockdown. FIG. 13D shows knockdown of cyclin-dependent kinase 5 (CDK5) by shRNA. FIG. 13E shows Western blot analysis and FIG. 13F shows quantification of CDK5 knockdown FIG. 13G show shRNA knockdown of topoisomerase 1 (Top1). FIG. 13H shows Western blot analysis and FIG. 13I shows quantification of knockdown of Top1 Whole cell lysates were resolved using SDS-PAGE and immunoblotted with anti-GFP and anti-β-actin. (n=3/group, p<0.01, *p<0.001). For FIGS. 13B, 13E, 13H Western immunoblot was performed with anti-GFP and anti-β-actin antibodies. FIGS. 13C, 13F, 13I, quantitative analysis of UBE3A-YFP unsilencing normalized to β-actin. scr: scrambled shRNA control, WT: wildtype; DMSO, (0.1% vehicle control); Topotecan (0.3 µM), PHA533533 (1.0 µM) (n=3/group, *p<0.05, **p<0.01).

FIGS. 14A-14E show that PHA533533 upregulates paternal Ube3a in vivo. FIG. 14A shows a schematic of the experimental design. FIGS. 14B-14D show immunohistochemistry of WT (FIG. 14B) or Ube3a$^{m+/pYFP}$ (FIGS. 14C-14E) mice GFP-stained sagittal brain sections at postnatal day 13 (P13) following intraperitoneal (IP) injection of saline (FIGS. 14B-14C) or 2 mg/kg of PHA533533 (FIG. 14D) at P11. FIG. 14E show high-magnification confocal micrographs of subcellular localization of paternal UBE3A-YFP in NeuN-positive hippocampal area CA3 neurons in Ube3a$^{m+/pYFP}$ mouse following IP injection of 2 mg/kg of PHA533533. UBE3A-YFP protein shows pronounced nuclear localization, consistent with the predominantly nuclear localization of UBE3A in mature neurons. Scale bars: 1 mm for (FIGS. 14B-14D) and 20 µm for (FIG. 14E).

DETAILED DESCRIPTION OF THE INVENTION

Figure 1A:
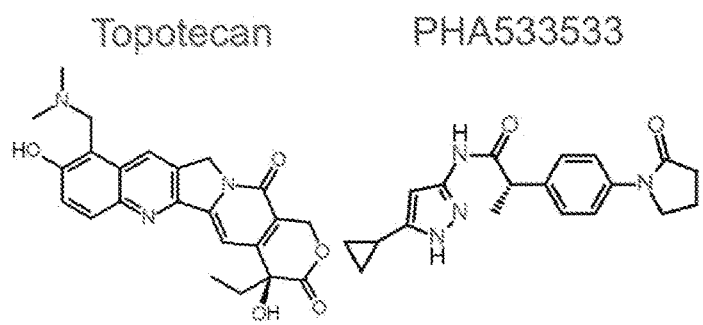
FIGS. 1A-1D show that PHA533533 and Compound X produce unsilencing of paternal Ube3a-YFP.

Particular aspects of this invention are explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure that do not depart from the instant invention.

Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, nucleotide sequences, amino acid sequences and other references mentioned herein are incorporated by reference in their entirety.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

All publications, patent applications, patents, nucleotide sequences, amino acid sequences and other references mentioned herein are incorporated by reference in their entirety.

As used herein, an "inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3" is a molecule (e.g., small molecule, e.g., a compound) that interferes with the activity of any of the listed proteins. In some embodiments, an inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3s may be PHA533533 or a derivative (e.g., metabolite thereof, e.g., salt thereof). PHA533533 is a synthetic compound originally designed for inhibiting cyclin-dependent kinase 2 (CDK2), but also inhibits CDK5 (Pevarello et al. *J. Med. Chem.* 2005:48(8): 2944-2956). Other inhibitors include, but are not limited to, (R)—N-(5-cyclopropyl-1H-pyrazol-3-yl)-2-(4-(2-oxopyrrolidin-1-yl)phenyl)propenamide, (S)—N-(5-cyclopropyl-1H-pyrazol-3-yl)-2-(4-(2-oxooxazolidin-3-yl)phenyl)propenamide [also referred to herein as P5-A4], or EPZ5676, as well as any other inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 now known or later identified. In some embodiments, one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 may be blood-brain barrier (BBB) permeable (e.g., a BBB permeant).

As used herein, a "genomic imprinting disorder" means any disorder caused by the mutation or deletion of a gene that is genetically imprinted, any disorder caused by alterations of the normal imprinting pattern, and/or any disorder caused by changes in gene dosage of an imprinted gene. In some embodiments, a genomic imprinting disorder of this invention may be Beckwith-Wiedemann syndrome, Silver-Russell syndrome, Prader-Willi syndrome, and/or Angelman syndrome. In some embodiments, a genomic imprinting disorder of this invention may be Angelman syndrome.

The present invention is based on the development of screening assays to identify substances (e.g., small molecules) that unsilence imprinted genes. This invention is further based on the unexpected discovery that PHA533533 can be used to treat Angelman syndrome.

Thus, in one embodiment, the present invention provides a method of inducing expression of Ube3a in a cell, comprising contacting the cell with an effective amount of one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3, thereby inducing expression of Ube3a in the cell. In some embodiments, the cell can be a central neuron, a peripheral neuron, a neuron differentiated from stem cells, a glial cell, an astrocyte, an oligodendrocyte, a microglial cell, and any combination thereof. In some embodiments, the cell can be in a subject (e.g., a human subject) and the Ube3a that is induced is the paternal allele of Ube3a. Such a subject can be a subject in which function of the maternal allele of Ube3a has been lost and Ube3a protein production is defective in the subject.

In certain embodiments of the present invention, the one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 has an efficiency, $E_{max}$, of at least about 1.5, 1.6, 1.7, 1.8, 1.9, 2.0, 2.1, 2.2, 2.3, 2.4, or 2.5 fold over control, or any value or range therein.

The present invention also provides various compositions. In some embodiments these compositions can be employed, e.g., in the methods described herein. Thus, the present invention provides a composition comprising, consisting essentially of and/or consisting of one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 and/or other compound of this invention (e.g., Compound X and/or PHA533533), which can be, for example, in a pharmaceutically acceptable carrier. "Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., Remington's Pharmaceutical Science; latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

It is further contemplated that the present invention provides a kit comprising, consisting essentially of and/or consisting of one or more compositions of this invention. It would be well understood by one of ordinary skill in the art that the kit of this invention can comprise one or more containers and/or receptacles to hold the reagents (e.g., one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3, e.g., Compound X, PHA533533, etc.) of the kit, along with appropriate buffers and/or diluents and/or other solutions and directions for using the kit, as would be well known in the art. The compositions and kits of the present invention can also include other medicinal agents, pharmaceutical agents, carriers and diluents, etc., in any combination. Actual methods of preparing such dosage forms are known, or will be apparent, to those skilled in this art.

In the kits of this invention, the compositions can be presented in unit\dose or multi-dose containers, for example, in sealed ampules and vials, and can be stored in a freeze-dried (lyophilized) condition requiring only the addition of a sterile liquid carrier, for example, saline or water-for-injection prior to use.

Symptomology of a genomic imprinting disorder and/or a disorder associated with epigenetic modification can include, but is not limited to, severe intellectual disabilities, seizures, EEG abnormalities, gait disturbances, disrupted sleep patterns, somatosensory deficits, profound language impairments, abnormal pain sensitivity, and balance abnormalities, which can be manifested singly and/or in any combination over time. Thus it is further contemplated that the present invention provides methods of treating one or more of these symptoms in any combination in a subject, comprising administering to the subject an effective amount of one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3.

A subject of this invention can be any animal in which genomic imprinting disorders occur and in particular embodiments, is a human subject, although nonhuman subjects [e.g., animal models of genomic imprinting disorders such as rodents (mice, rats, hamsters, guinea pigs, etc.), pigs, non-human primates] are included within the present invention.

A subject of this invention can be "in need of" the methods of the present invention, e.g., because the subject has, or is believed at risk for, a genomic imprinting disorder including those described herein, such as Angelman syndrome and/or is a subject that would benefit from the methods of this invention. For example, a subject in need of the methods of this invention can be, but is not limited to, a subject diagnosed with, having or suspected to have, or at risk of having or developing a genomic imprinting disorder (e.g., Angelman syndrome).

The term "therapeutically effective amount" or "effective amount," as used herein, refers to that amount of an inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 and/or other compound and/or composition of this invention that imparts a modulating effect, which, for example, can be a beneficial effect, to a subject afflicted with a condition (e.g., a disorder, disease, syndrome, illness, injury, traumatic and/or surgical wound), including improvement in the condition of the subject (e.g., in one or more symptoms), delay or reduction in the progression of the condition, delay of the onset of the condition, and/or change in clinical parameters, status or classification of a disease or illness, etc., as would be well known in the art.

For example, a therapeutically effective amount or effective amount can refer to the amount of an inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 and/or other compound and/or composition of this invention that improves a condition in a subject by at least about 5%, e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%.

"Treat" or "treating" or "treatment" refers to any type of action that imparts a modulating effect, which, for example, can be a beneficial effect, to a subject afflicted with a condition (e.g., disorder, disease, syndrome, illness, traumatic or surgical wound, injury, etc.), including improvement in the condition of the subject (e.g., in one or more symptoms), delay or reduction in the progression of the condition, delay of the onset of the condition, and/or change in clinical parameters, disease or illness, etc., as would be well known in the art.

By the terms "treat," "treating" or "treatment of" (or grammatically equivalent terms), it is also meant that the severity of the subject's condition is reduced or at least partially improved or ameliorated and/or that some alleviation, mitigation or decrease in at least one clinical symptom is achieved and/or there is a delay in the progression of the condition and/or delay of the onset of a disease or disorder.

By "prevent," "preventing" or "prevention" is meant to avoid or eliminate the development and/or manifestation of a pathological state and/or disease condition or disorder or status in a subject.

Exemplary modes of administration of one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 (e.g., Compound X, PHA533533, etc.) and/or other compound and/or composition of this invention can include oral, rectal, transmucosal, topical, intranasal, inhalation (e.g., via an aerosol), buccal (e.g., sublingual), vaginal, intrathecal, intracerebroventricular, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration, and the like, as well as direct tissue or organ injection (e.g., to liver, skeletal muscle, cardiac muscle, diaphragm muscle or brain). The most suitable route in any given case will depend on the nature and severity of the condition being treated and on the nature of the particular therapeutic compound and/or composition that is being used.

For injection, the carrier will typically be a liquid. For other methods of administration, the carrier may be either solid or liquid. For inhalation administration, the carrier will be respirable, and will typically be in solid or liquid particulate form.

Dosages of the one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 and/or other compound(s) of this invention to be administered to a subject will depend upon the mode of administration, the disease or condition to be treated, the individual subject's condition, the particular therapeutic compound and/or composition, and any other agents being administered to the subject and can be determined in a routine manner according to methods well known in the art. An exemplary dosage range for a human subject is from about 0.001 mg/kg/day to about 500 mg/kg/day. In some embodiments, the dosage range can be from about 0.01 mg/kg/day to about 100 mg/kg/day and in some embodiments, the dosage range can be from about 0.1 mg/kg/day to about 10 mg/kg/day. For example, in some embodiments, the dosage range can be from about 0.1 mg/kg/day to about 2 mg/kg/day, about 1.5 mg/kg/day to about 8 mg/kg/day, about 200 mg/kg/day to about 450 mg/kg/day, or about 1 mg/kg/day to about 5 mg/kg/day or any value or range therein, e.g., about 1 mg/kg/day, about 2 mg/kg/day, about 5 mg/kg/day, about 10 mg/kg/day, about 50 mg/kg/day, about 100 mg/kg/day, about 250 mg/kg/day, or about 450 mg/kg/day.

A nonlimiting example of a method of treating Angelman syndrome in a human subject comprises administering to the subject (e.g., in utero, perinatally, postnatally, during infancy, during childhood, during adolescence, during teen years, during early adulthood, during middle adulthood, during late adulthood and any combination thereof), a dose of one or more inhibitor of CDK5, DOT1L, ATXR5, ASH1L, CBP, CDK2, CDK5, CDK6, CDK8, CDK9, CDK16, CDKL1, CDKL3, EHMT1, EHMT2, EZH2, KMT5C, SETD7, SMYD1, and/or SMYD3 of this invention in the range of about 0.01 nmole to about 100 mmole by an intrathecal and/or intracerebroventricular route, or any value or range therein. For example, in some embodiments the dose could be in the range of about 0.1 nmole to about 2 nmole, about 1.5 nmole to about 10 mmole, about 2 nmole to about 5 mmole, about 1 nmole to about 75 nmole, about 50 mmole to about 100 mmole, or about 0.1 nmole, about 0.5 nmole, about 1 nmole, about 2 nmole, about 5 nmole, about 10 nmole, about 25 nmole, about 50 nmole, about 75 nmole, about 100 nmole, about 250 nmole, about 500 nmole, about 750 nmole, about 1 mmole, about 2 mmole, about 5 mmole, about 10 mmole, about 25 mmole, about 50 mmole, about 75 mmole, or about 100 mmole. In some embodiments, the route of administration could be intrathecal and/or intracerebroventricular and the dose could be in the range of about 0.01 mg/kg to about 100 mg/kg or any value or range therein, and in some embodiments could be about 0.1 mg/kg to about 10 mg/kg or any value or range therein. For example, in some embodiments the dose could be in the range of about 0.1 mg/kg to about 2 mg/kg, about 1.5 mg/kg to about 10 mg/kg, about 2 mg/kg to about 5 mg/kg, about 1 mg/kg to about 75 mg/kg, about 50 mg/kg to about 100 mg/kg, or about 0.1 mg/kg, about 0.5 mg/kg, about 1 mg/kg, about 2 mg/kg, about 5 mg/kg, about 10 mg/kg, about 25 mg/kg, about 50 mg/kg, about 75 mg/kg, about 100 mg/kg.

In some embodiments, a single administration of a therapeutic compound and/or composition of this invention may be effective. In other embodiments, more than one administration (e.g., two, three, four or more administrations) of the therapeutic compound and/or composition may be employed to achieve the desired result over a period of various intervals, e.g., hourly, daily, weekly, monthly, yearly, etc.

The present invention will now be described with reference to the following examples. It should be appreciated that these examples are for the purposes of illustrating aspects of the present invention, and do not limit the scope of the invention as defined by the claims provided herein.

EXAMPLES

Example 1

There are numerous mechanistic possibilities for reactivating paternal UBE3A expression, such as (1) increasing methylation to repress UBE3A-ATS, (2) powerfully driving UBE3A expression to outcompete UBE3A-ATS, or (3) directly repressing UBE3A-ATS. Any approach that unsilences the dormant paternal UBE3A allele in neurons would offer a therapeutic opportunity for AS.

Because the paternally-inherited copy of UBE3A is intact but epigenetically silenced in most mature neurons, maternal allele loss of UBE3A largely depletes functional UBE3A protein in the brain. This unique epigenetic biology suggests that activating the dormant paternal allele of UBE3A could provide a transformative treatment for AS. The feasibility of this approach was previously demonstrated by showing that topoisomerase inhibitors, such as topotecan, can successfully reactivate the paternal Ube3a allele in neurons from AS model mice. However, challenges with toxicities and central nervous system (CNS) bioavailability have limited the potential for topoisomerase inhibitors to treat AS, raising a quest to identify novel small molecule Ube3a unsilencers. Herein is reported a high content screen, which revealed two small molecules, PHA533533 and Compound X, that effectively reactivate paternal Ube3a in neurons from AS model mice. These compounds do not produce Ube3a unsilencing through topoisomerase inhibition, suggesting they act through novel mechanisms of unsilencing that are shown to possibly involve the simultaneous inhibition of cyclin-dependent kinase 5 (CDK5) and disruptor of telomeric silencing 1-like (DOT1L). This study provides novel small molecule approaches and potential mechanisms to unsilence paternal Ube3a, and hence, to treat AS. PHA533533 is an inhibitor of cyclin-dependent kinase 2 and 5 (CDK2 and CDK5) (Pevarello et al. *J Med Chem* 2005 48(8):2944-2956). Molecular predictions and subsequent preliminary experiments suggest that these two compounds might be producing their effects through shared action of inhibiting CDK5 and DOT1L [Disruptor of telomeric silencing 1-like; histone H3 lysine 79 (H3K79) specific methyltransferase]. The results of this study provide new therapeutic possibilities for treating AS that could be advanced for preclinical testing of safety and efficacy in mouse models of AS and further vetted using AS patient-derived neuronal cell lines.

Animals: All animal experiments were conducted under the Institutional Animal Care and Use Committee protocol approved by the University of North Carolina School of Medicine. To generate paternal YFP-tagged mice (Ube3a$^{m+/pYFP}$) for high content screen and drug validation, heterozygote Ube3a-YFP males were crossed with wildtype (WT) females. Ube3a$^{m+/p-}$ females were also crossed with WT males to generate AS model mice (Ube3a$^{m-/p+}$). Mice were housed on a 12 hr:12 hr light/dark cycle and given ad libitum access to food and water. Embryonic male and female mice were randomly used for cortical neuronal isolation and culture.

Chemistry and drug preparation: Topotecan hydrochloride and EPZ5676 were purchased from Cayman Chemicals. Dinaciclib and PHA793887 were purchased from Selleck-Chem. Amsacrine and ICRF-193 were purchased from Sigma Aldrich. Synthesis of PHA533533 and four analogues has been previously described. Individual compounds in the Pfizer chemogenetic library were pre-dissolved in DMSO. The drug plates for screening were prepared at a final concentration of 1 µM. Cherry-picked compounds listed above were freshly prepared in DMSO as a 10 mM stock and further diluted for the final experimental concentration in culture medium or enzyme assays.

Cell culture and drug treatment: Primary cortical neurons were isolated and cultured by following established protocol. Briefly, cortical neurons were isolated from embryos (E13.5-15.5) carrying paternal Ube3a-YFP (Ube3a$^{m+/pYFP}$) or maternal deletion of Ube3a (Ube3a$^{m-/p+}$). Isolated cortical neurons were plated onto 384-well plates coated with poly-D-lysine ($2.0\times10^4$ cell/well) for high-content imaging analysis or 6-well plates coated with poly-D-lysine ($1.0\times10^6$ cells/well) for molecular and biochemical assays (western blot analysis, quantitative RT-PCR, and shRNA knockdown). Cultured neurons were maintained for 7 days, replacing medium every 3-4 days. On day 7 (DIV 7), the indicated compounds were added at 0.3-1 µM to neurons for 72 hr to unsilence paternal Ube3a or Ube3a-YFP. All drug concentrations are provided in figures.

Fluorescence immunocytochemistry and high content imaging analysis: Fluorescent immunocytochemistry and high content imaging analysis were performed by following previously described protocols with slight modifications. After 72 hr drug treatment, the neurons were fixed with 4% paraformaldehyde in 1×PBS at room temperature for 10 min. After brief washing with 1×PBS three times, neurons were permeabilized with 1% Triton-X 100 in 1×PBS at room temperature for 15 min, followed by blocking with 5% normal goat serum in 0.1% Triton-X 100 in 1×PBS at room temperature. 60 min after blocking, neurons were incubated with primary antibody, rabbit anti-GFP (1:1000, Novus Biologicals), at 4° C. overnight. Neurons were then briefly washed with 1×PBS followed by incubation with secondary antibody, goat anti-rabbit Alexa Fluor 488 (1:500, Thermo Fisher/Invitrogen) and Hoechst 33342 (Thermo Fisher), at room temperature for 60 min. Following secondary antibody incubation, neurons were washed with 1×PBS and fluorescent images were acquired using a BD Pathway 855 bioimager. All acquired images were analyzed by CellProfiler.

Cytotoxicity test: Cytotoxicity of drugs was tested in cultured mouse cortical neurons in vitro. The manufacturer's protocol was followed to measure luminescence proportional to the number of dead cells using Cyto Tox-Glo assay (Promega). 72 hr after drug treatment, AAF-Glo substrates were directed added to the drug-treated (or 0.1% DMSO vehicle-treated) cortical neurons and incubated them at room temperature for 15 min. Luminescence produced by dead-cell protease activity was then measured.

shRNA knockdown and western blot analysis: Lentiviral shRNAs of Top1 (TRCN0000011884), CDK2 (TRCN0000023146), and CDK5 (TRCN0000009520) were generated using previously described techniques. Cultured cortical neurons were infected at DIV 3 and virus was removed the next day (DIV 4). Neurons were further cultured and treated at DIV 10 with vehicle (0.1% DMSO) or the indicated compounds. To perform western blot analysis, the cultured neurons from 6-well plates were harvested and total protein was extracted with protein extraction buffer 72 hr after drug treatment, Bradford assays were performed to measure protein concentration, and 30 μg of total protein was loaded for Bis-polyacrylamide gel electrophoresis (Bio-Rad). Electrophoresed proteins were transferred to nitrocellulose membrane (0.45 μm, Bio-Rad). Membranes were blocked with 5% non-fat milk in 1×TBS-T at room temperature for 30 min followed by overnight 4° C. incubation with primary antibodies [rabbit anti-GFP (1:1000, Novus Biologicals), rabbit anti-Ube3a (1:1000, Bethyl Lab), rabbit anti-H3K79Me2 (1:1000, Abcam), rabbit anti-H3K79Me3 (1:1000, Abcam), and mouse anti-β-actin (1:5000, Sigma)]. The next day, the immunoblot membranes were rinsed with 1×TBS-T three times and incubated with HPR-conjugated secondary antibodies for 1 hr at room temperature (goat anti-rabbit @ 1:1000 or goat anti-mouse @ 1:1000, Vector Labs). Following secondary antibody incubation, the membranes were rinsed (4-5 times) with 1×TBS-T at room temperature for 1 hr and ECL (Bio-Rad) was used to visualize detected proteins using an Amersham Imager 600 (AI600, GE Life Sciences).

Quantitative real-time PCR and topoisomerase-based DNA relaxation assay: Quantitative real-time PCR (qPCR) was performed using previously reported protocols. Briefly, total RNA was extracted from cultured cortical neurons carrying Ube3a$^{m+/pYFP}$ after drug treatment using Direct-zol RNA kit (Zymo Research). cDNA pool was synthesized using 2 μg of total RNA and qScript cDNA Supermix (Quantabio). qPCR was performed using SsoAdvanced Universal SYBR green Supermix (Bio-rad). The primer sets were β-actin (forward, 5'-agagctacgagctgcctgac-3', SEQ ID NO:1; reverse, 5'-agcactgtgttggcgtacag-3, SEQ ID NO:2), YFP (forward, 5'-acatgaagcagcacgacttct-3', SEQ ID NO:3; reverse, 5'-gacgttgtggctgttgtagttgta-3', SEQ ID NO:4), Ube3a-ATS (forward, 5'-acagaacaataggtcaccaggtt-3', SEQ ID NO:5; reverse, 5'-aagcaagactgttcacctcat-3', SEQ ID NO:6), Snrpn (forward, 5'-ttggttctgaggagtgatttgc-3', SEQ ID NO:7; reverse, 5'-ccttgaattccaccaccttg-3', SEQ ID NO:8), and Snord116 (forward, 5'-ggatctatgatgattcccag-3', SEQ ID NO:9; reverse, 5'-ggacctcagttccgatga-3', SEQ ID NO:10). qPCR was performed using QuantStudio thermocycler (Thermo Fisher) with the following conditions: 95° C. for 5 min and followed by 40 cycles of 95° C. 10 sec, 60° C. 1 min. Relative quantity (RQ) was calculated after normalized ΔΔCt was calculated. Topoisomerase (Top)-based DNA relaxation assays were performed to test whether the drugs inhibited Top1, Top2a, and Top2b. Top1 and Top2a assay kits were purchased from TopoGEN, and Top2b enzyme was purchased from Inspiralis. All Top-based assays followed manufacturer protocols.

Statistical analysis: One-way ANOVA with Dunnett's multiple comparison test was performed to determine significant changes in unsilencing of paternal Ube3a-YFP or Ube3a. Two-way ANOVA with Bonferroni correction for multiple comparisons was performed to determine significant differences in $EC_{50}$, $E_{max}$, and $LC_{50}$.

Figure 1B:
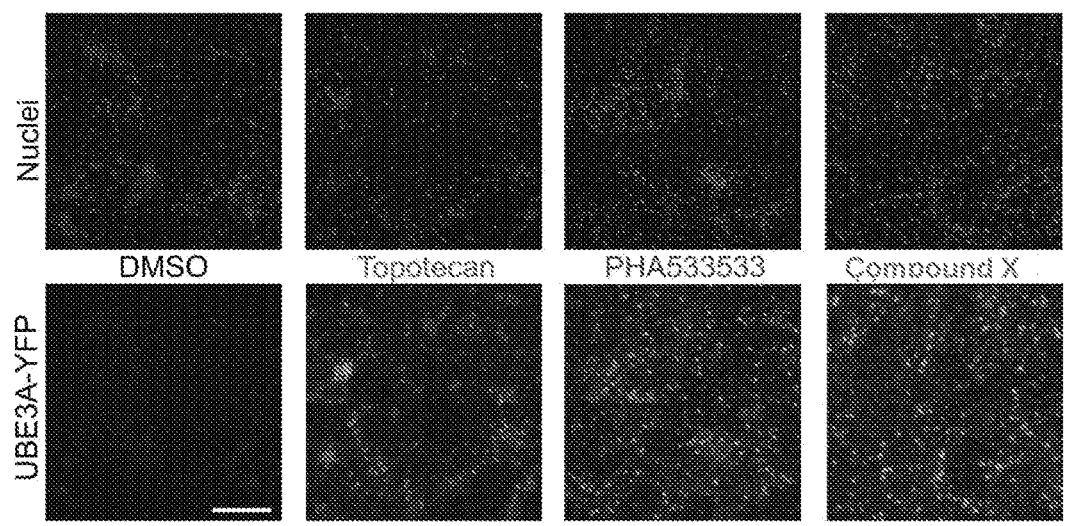
Figure 1C:
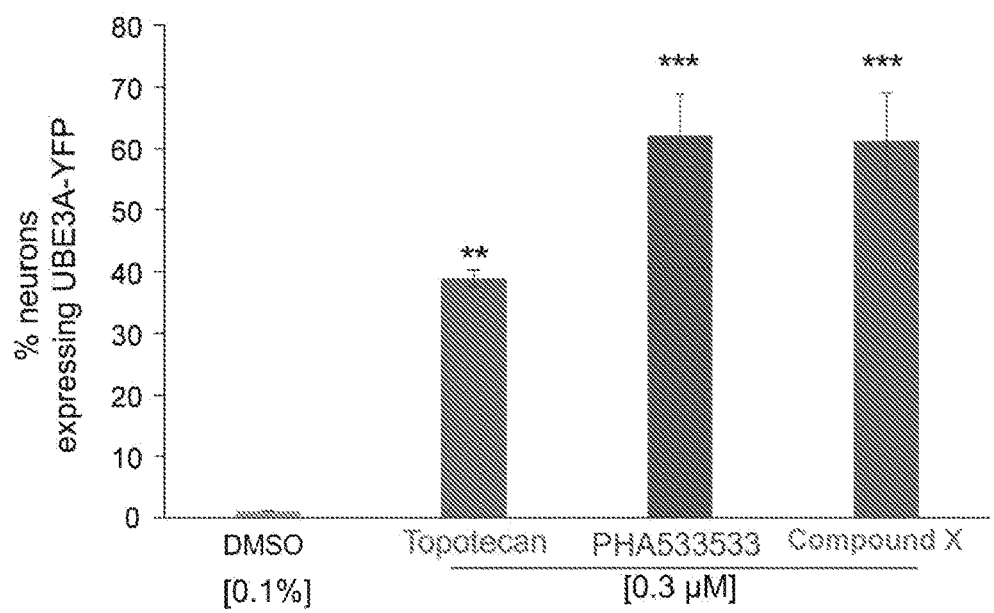
Figure 1D:
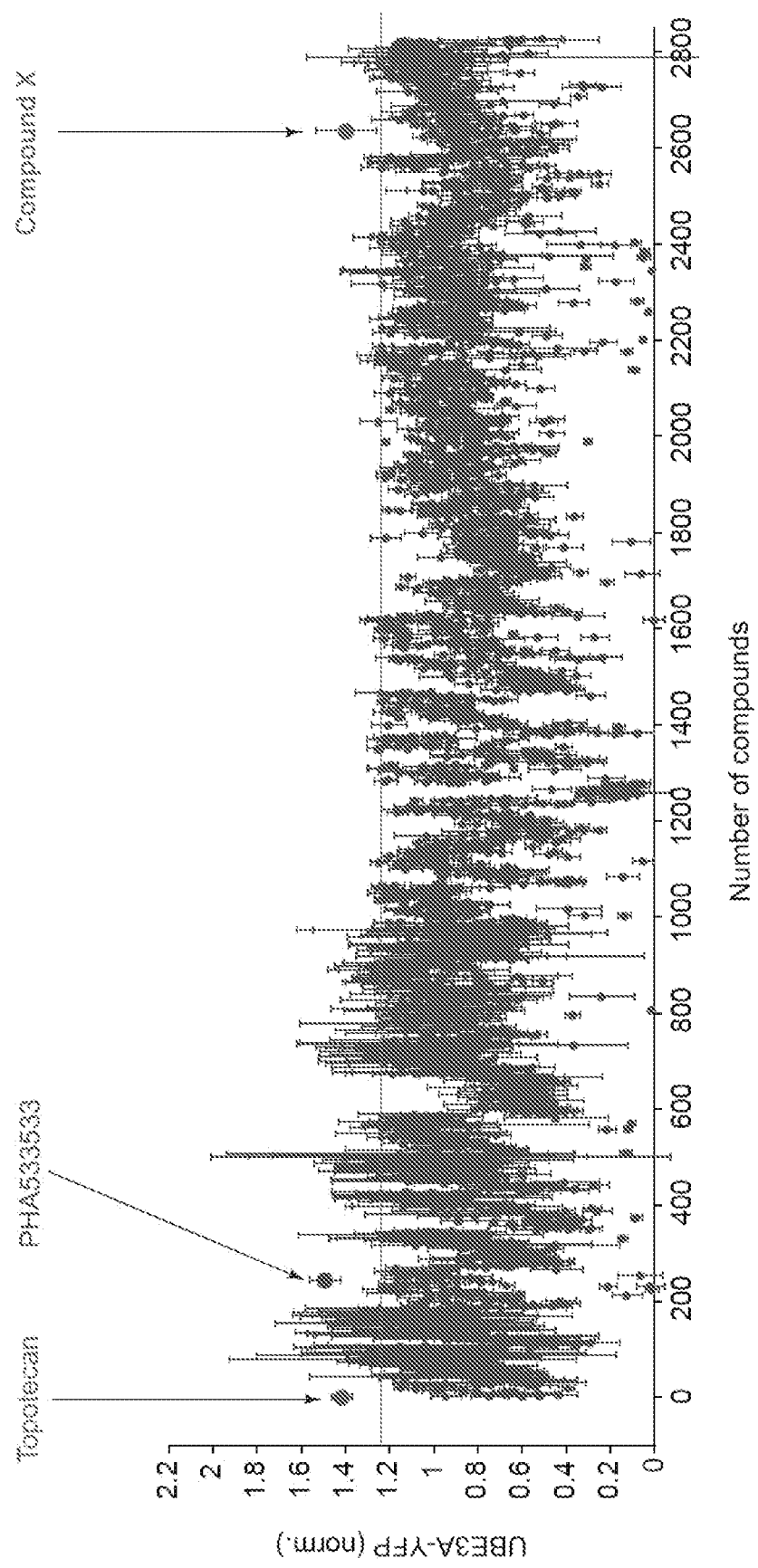

PHA533533 and Compound X are novel Ube3a unsilencers: A high-content drug screen that was previously developed for primary neurons (Huang et al. Nature 2011 481 (7380):185-189) was employed to identify novel classes of unsilencers. This screen leverages mice that have a paternal Ube3a-YFP knock-in, allowing for fluorescence-based identification of paternal Ube3a expression in cultured neurons from these mice. Through screening >2,800 compounds in the Pfizer chemogenetic library, two small molecules, PHA533533 and Compound X, were found that effectively unsilenced paternal Ube3a-YFP (FIG. 1A-1D). Importantly, PHA533533 and Compound X are not structural analogues, nor are they structural analogues to topotecan (FIG. 1A). As a negative control, there was minimal paternal UBE3A-YFP protein expressed in cultured cortical neurons in the presence of 0.1% DMSO (vehicle control) (FIG. 1B). As an important positive control, topotecan unsilenced paternal UBE3A-YFP as previously reported (Huang et al) (FIG. 1B). In quantifying the results across sample runs (n=4), topotecan (37.3±3.7%), PHA53533 (63.7±14.3%), and Compound X (61.2±15.7%) all significantly increased the percent of neurons expressing UBE3A-YFP above threshold compared to DMSO control (0.03±0.004%) (FIG. 1C). PHA533533 was originally designed for inhibiting cyclin-dependent kinase 2 (CDK2), however it also inhibits CDK5. These data suggest that PHA533533 and Compound X may unsilence paternal Ube3a through a previously undescribed mechanism.

Figure 2A:
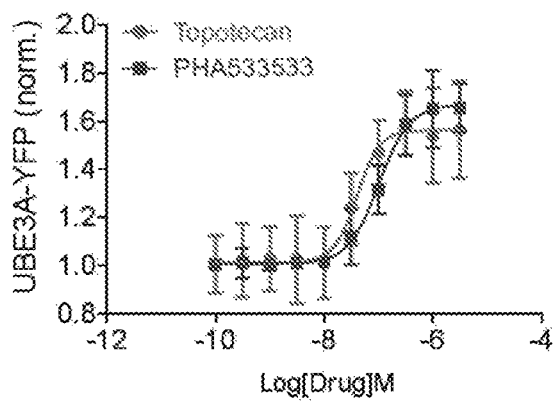
FIGS. 2A-2E show pharmacological profiles of PHA533533 and Compound X in unsilencing paternal Ube3a-YFP in vitro.
Figure 2B:
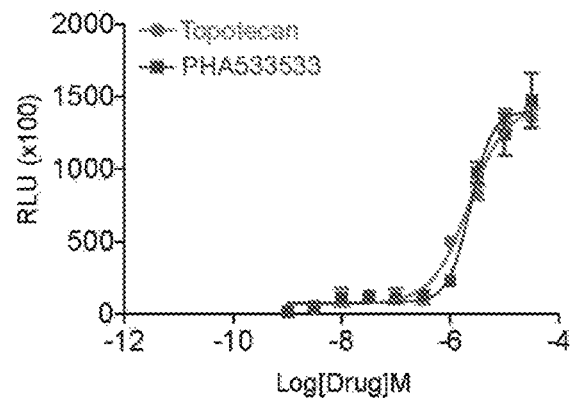
Figure 2B:
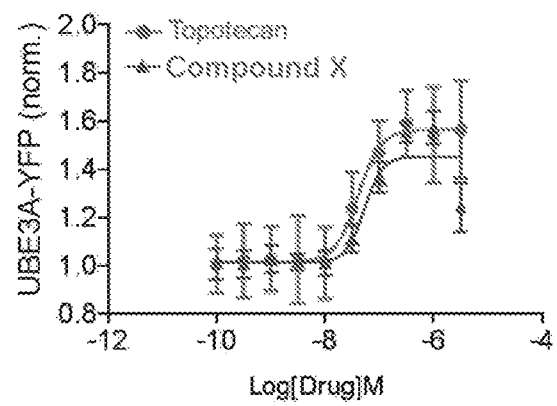
Figure 2B:
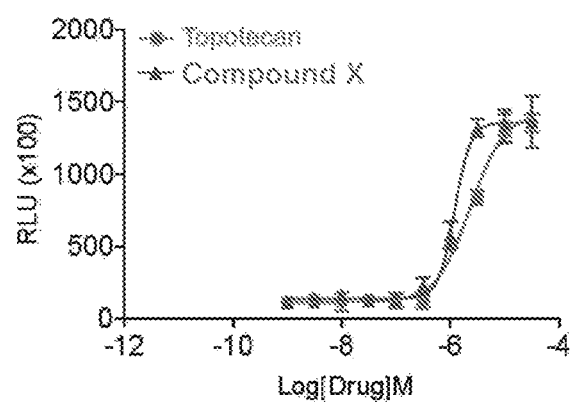
Figure 2C:
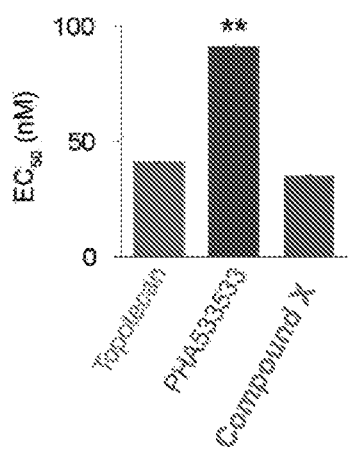
Figure 2D:
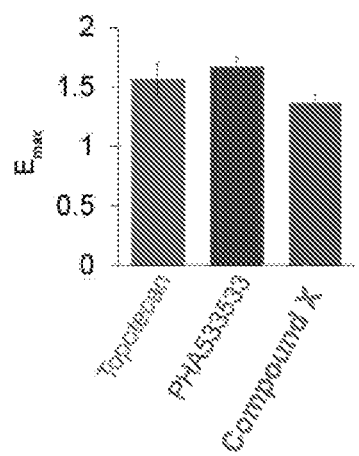
Figure 2E:
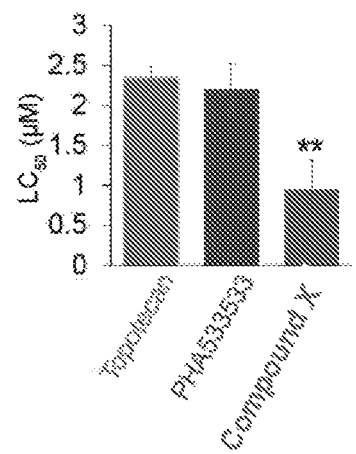

To understand the pharmacological properties of these novel unsilencers, their $EC_{50}$ (effective dose producing relative 50% of normalized intensity), $E_{max}$ (maximum effectiveness in normalized intensity), and $LC_{50}$ (lethal dose required to kill 50% of cell population) were measured. Dose response curves indicated that the potency ($EC_{50}$) of PHA533533 is >2-fold higher than that of topotecan, whereas Compound X shared a similar potency with topotecan (FIGS. 2A and 2C). On the other hand, the efficacy ($E_{max}$) of the three drugs are similar (FIGS. 2A and 2D). Cytotoxicity tests revealed a comparable $LC_{50}$ for PHA533533 and topotecan, while the $LC_{50}$ of Compound X is ~2-fold less than the other two compounds (FIGS. 2B and 2E). These data suggest that the novel unsilencers are drug-like small molecules that could be developed as potential AS therapeutics.

Figure 3B:
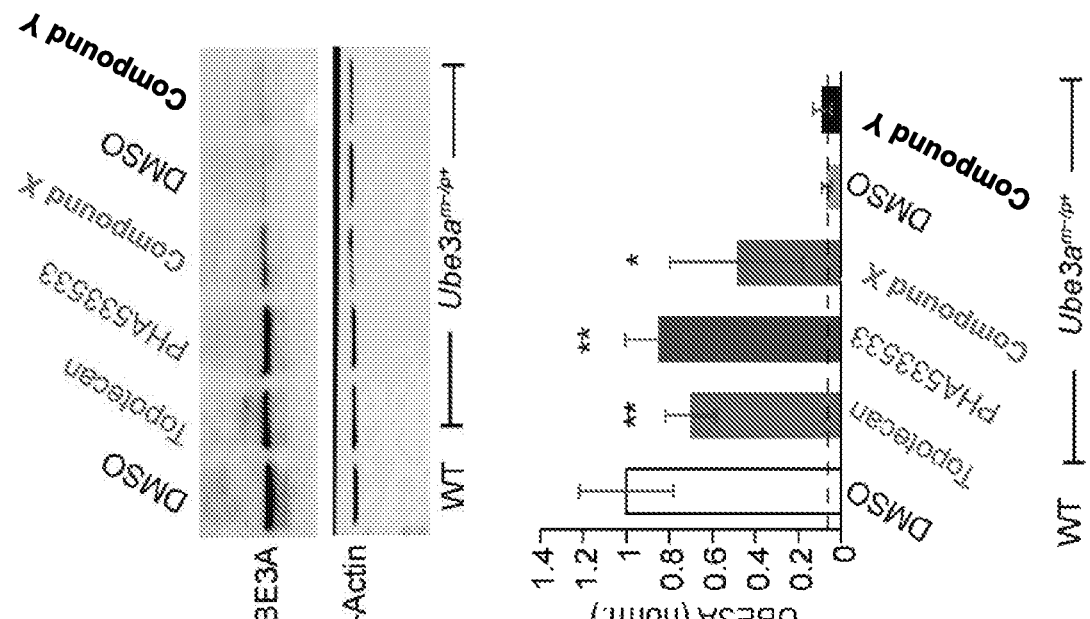
FIGS. 3A-3G show PHA533533 and Compound X treatments downregulate the Ube3a-ATS and produce UBE3A protein from the paternal allele.
Figure 3A:
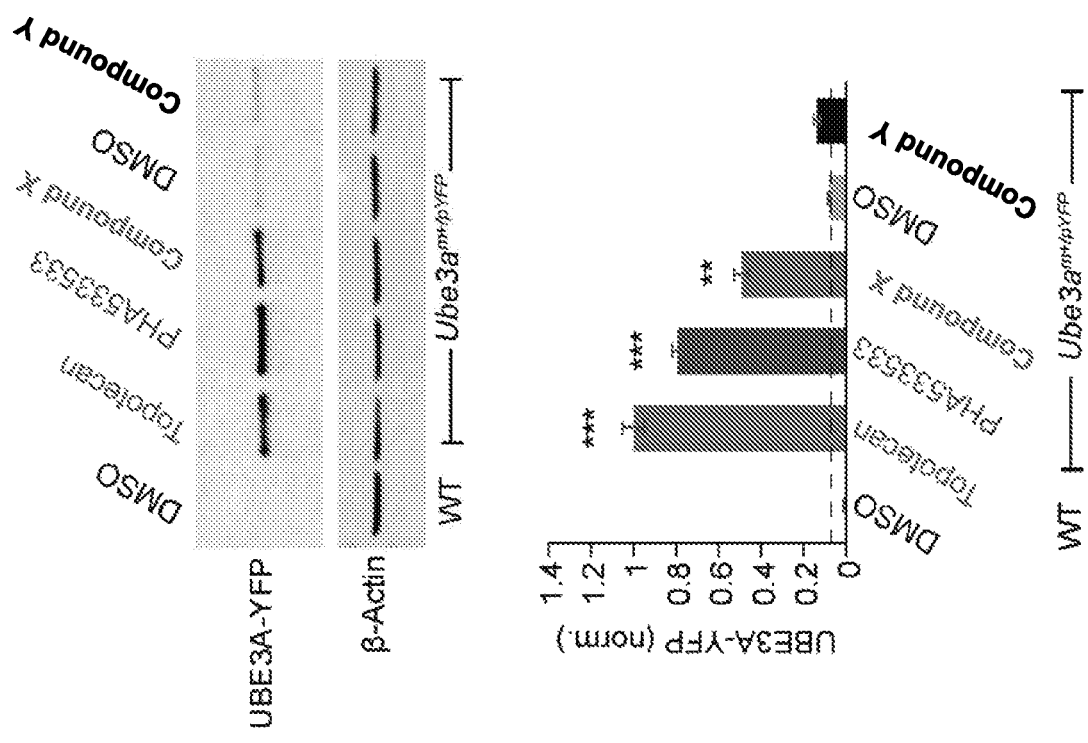

PHA533533 and Compound X downregulate Ube3a-antisense transcript and unsilence paternal Ube3a in AS model mice (Ube3a$^{m-/P+}$) To exclude the possibility that image-based results were due to fluorescence artifacts (e.g., intrinsic fluorescence in compounds), western blots were performed to analyze UBE3A-YFP protein expression from drug- and vehicle-treated primary neurons from WT or paternal Ube3a-YFP mice. The opportunity was also taken to test the effects of control Compound Y. No UBE3A-YFP signal was detected in neurons from WT mice, demonstrating specificity of our GFP antibody towards YFP (FIG. 3A). Paternal UBE3A-YFP was marginally detectable in 0.1% DMSO treated Ube3a$^{m+/pYFP}$ neurons, probably due to incomplete silencing of paternal Ube3a-YFP in these immature neurons and/or to small populations of glial cells that normally express Ube3a biallelically. These results show that PHA533533 and Compound X increased UBE3A-YFP protein to levels approaching that of topotecan (FIG. 3A). However, control Compound Y did not unsilence paternal UBE3A-YFP.

Figure 7A:
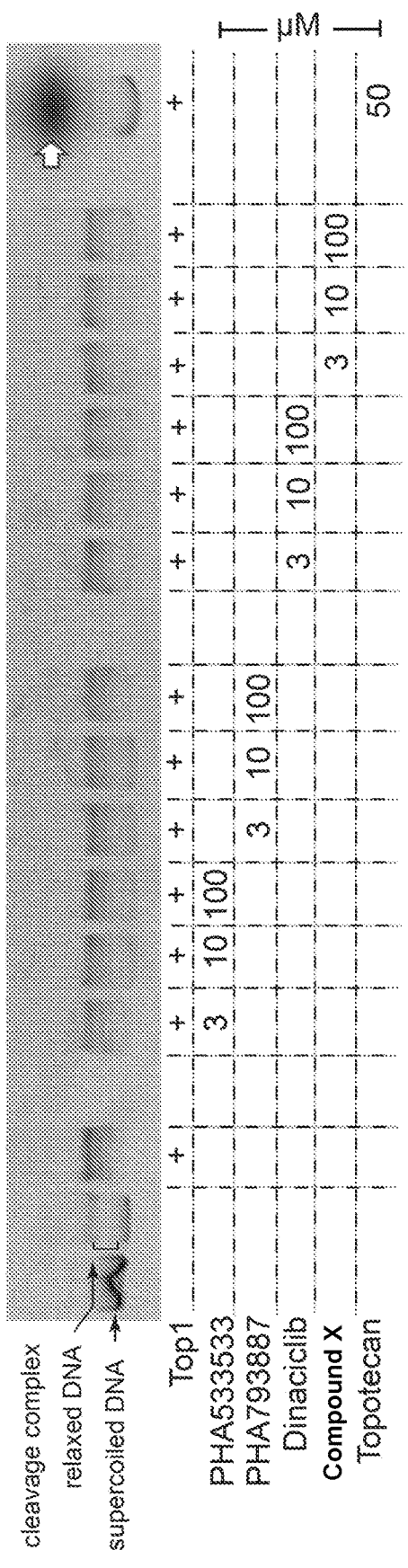
FIGS. 7A-7B show DNA relaxation assays evaluating relative inhibition of Top1 (FIG. 7A) and Top2b (FIG. 7B) via treatment with PHA533533, PHA793887, Dinaciclib, Compound X, or Topotecan.
Figure 7B:
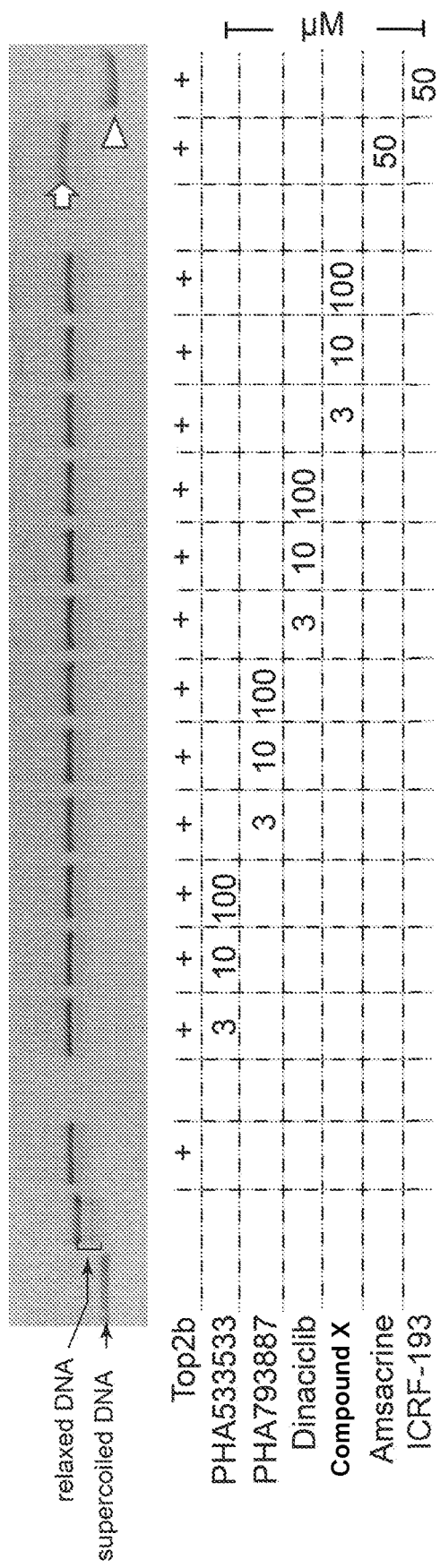

To exclude the possibility that the results were somehow an artifact of the Ube3a-YFP knock-in transgene, western blots were performed to analyze UBE3A protein expression from drug- and vehicle-treated primary neurons from WT or AS model mice (Ube3a$^{m+/p+}$) This also provided the opportunity to assess the extent to which the unsilencing agents restored UBE3A protein to WT levels. Topotecan, PHA533533, and Compound X unsilenced paternal UBE3A at levels that approached that of UBE3A levels in DMSO-treated neurons from WT mice (FIG. 3B). Little paternal UBE3A was observed when treating neurons from AS model mice with control Compound Y, similar to what was observed in DMSO-treated AS neurons. Two enantiomer pairs of PHA533533 structural analogues were also tested (FIG. 3G), and it was found that neither 1 μM drug treatments (FIG. 7), nor dose-response tests, of these compounds could produce appreciable increases in paternal UBE3A-YFP or paternal UBE3A.

Figure 3C:
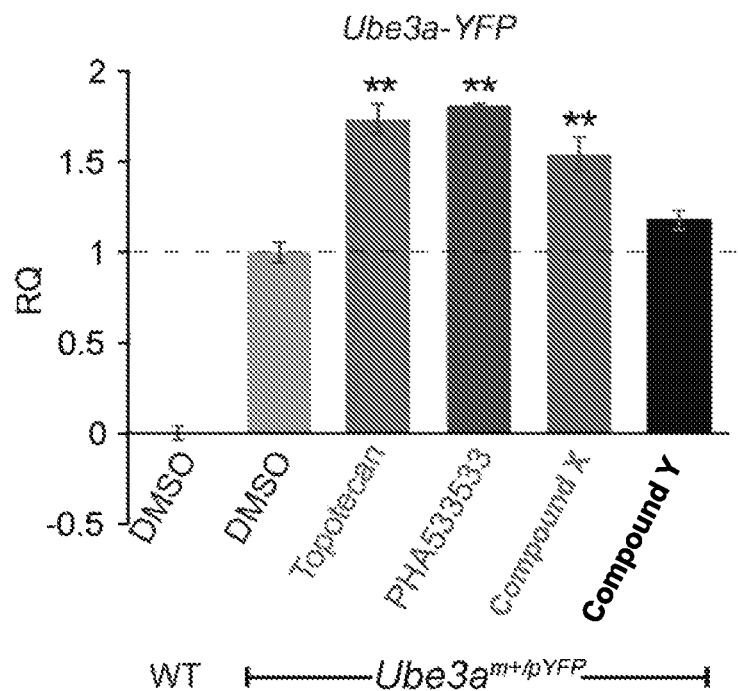
Figure 3D:
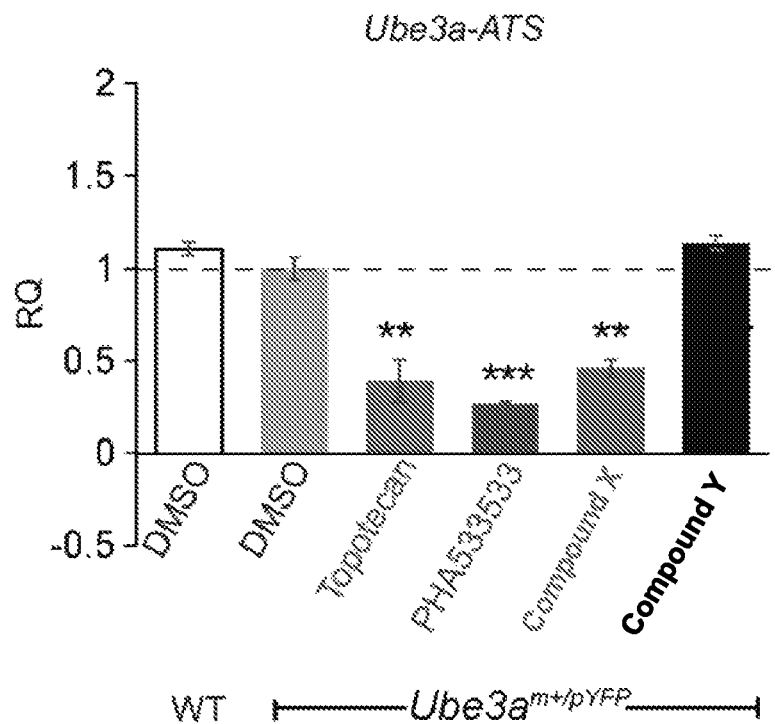
Figure 3E:
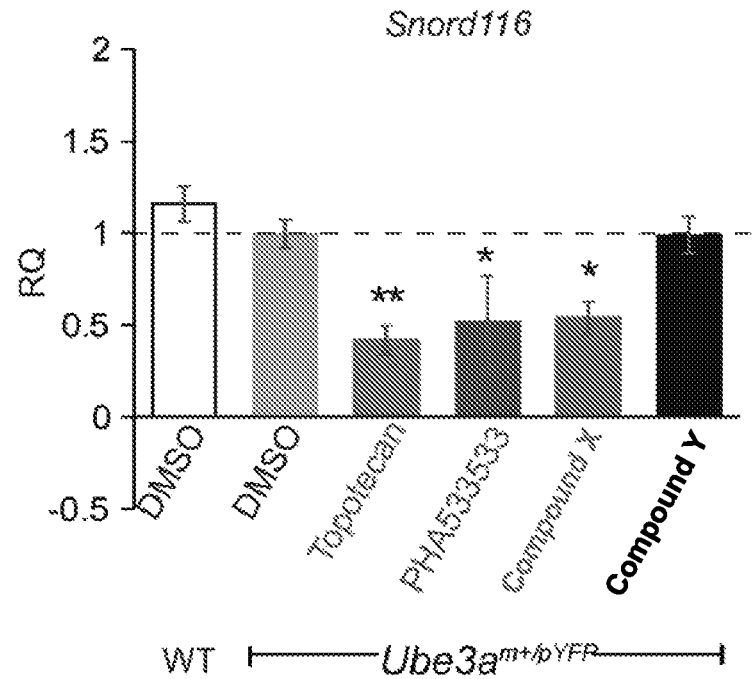
Figure 3F:
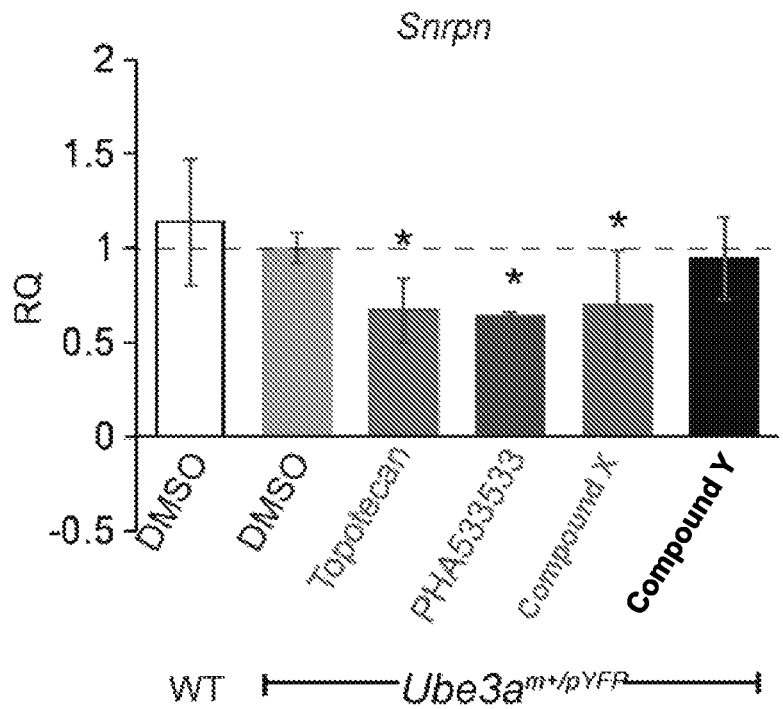
Figure 3G:
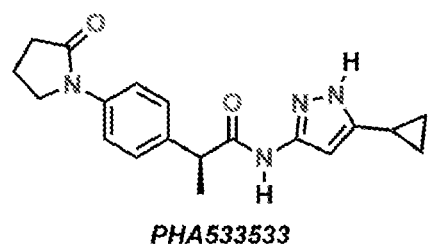
Figure 3G:
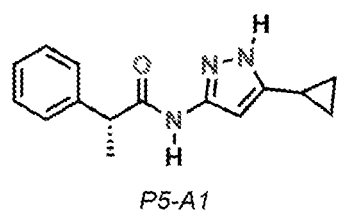
Figure 3G:
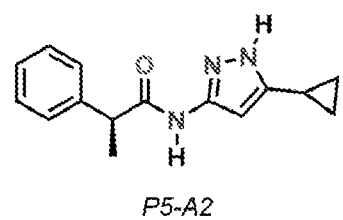
Figure 3G:
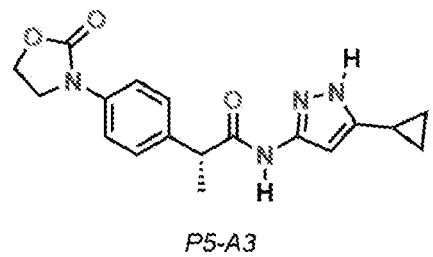
Figure 3G:
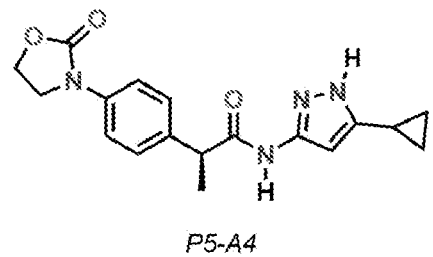

Since Ube3a-ATS is necessary for epigenetically silencing paternal Ube3a, interference of Ube3a-ATS provides a mechanistic possibility to produce paternal Ube3a unsilencing as previously shown for topotecan. To test this hypothesis, mRNA levels in DMSO- and drug-treated neurons were quantified. As expected, mRNA of Ube3a-YFP was upregulated by PHA533533, Compound X, and topotecan, but not by control Compound Y (FIG. 3C). Furthermore, Ube3a-ATS mRNA was significantly decreased by PHA533533, Compound X, and topotecan (FIG. 3D). The observed downregulation of Ube3a-ATS led to tests whether the novel unsilencers affected other genes upstream of this locus. Snord116 and Snrpn were also decreased by PHA533533, Compound X, and topotecan, but not by control Compound Y (FIGS. 3E and 3F). Taken together, these data indicate that downregulation of Ube3a-ATS by PHA533533 and Compound X may mediate unsilencing of paternal Ube3a.

Figure 4A:
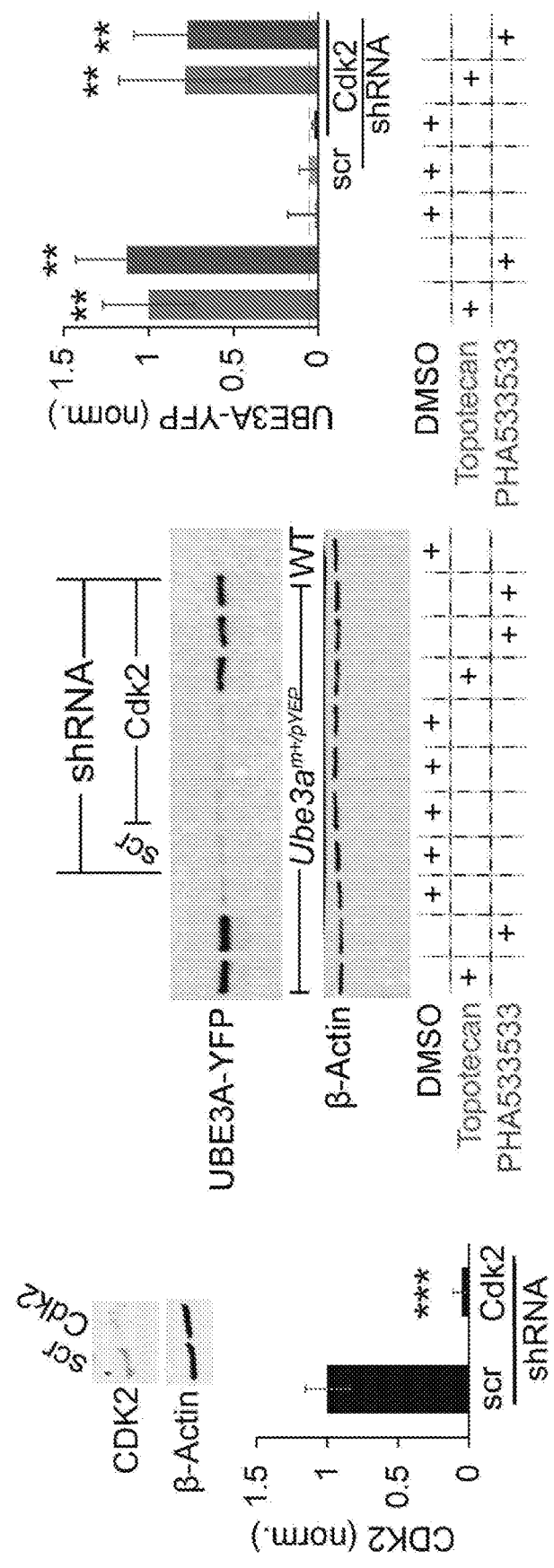
FIGS. 4A-4C show knockdown of established PHA533533 and Compound X molecular targets is not sufficient to dramatically unsilence paternal Ube3a-YFP.
Figure 4B:
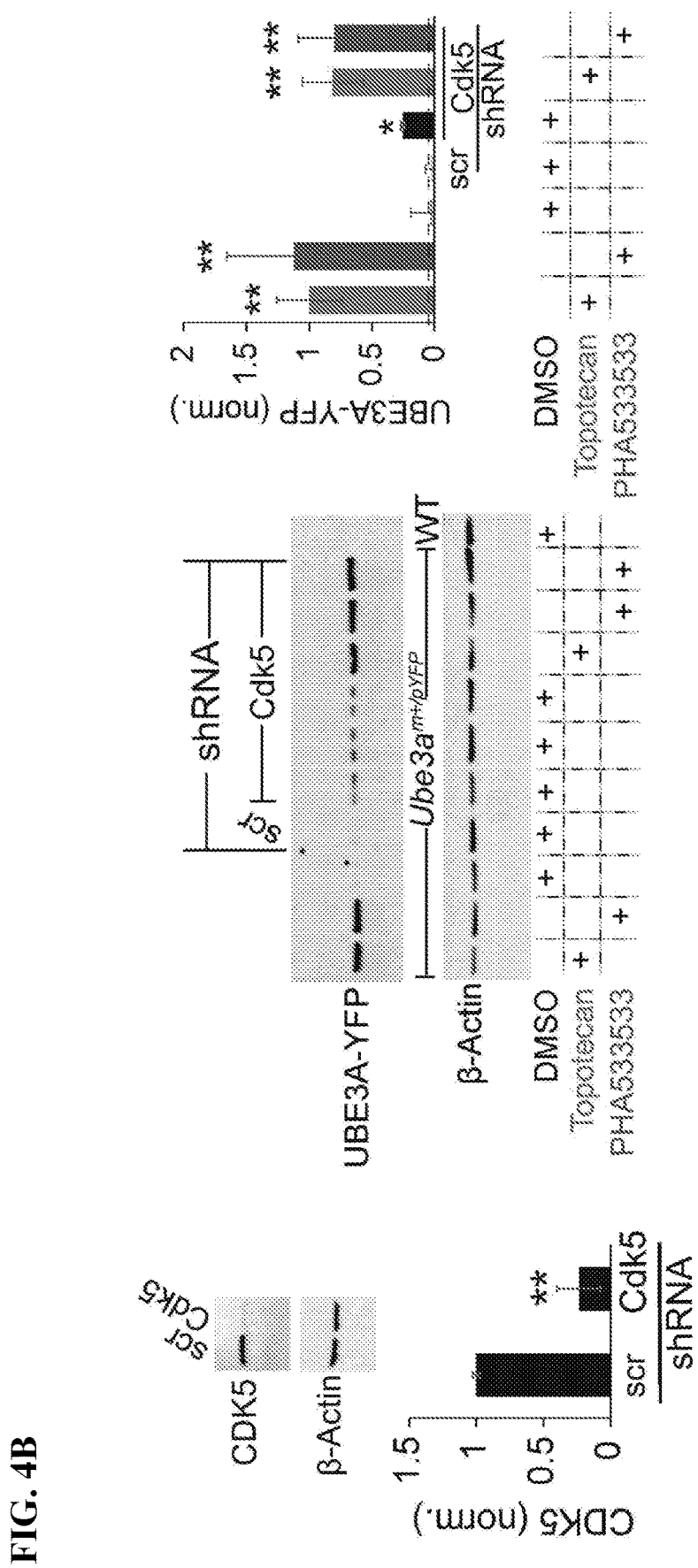
Figure 4C:
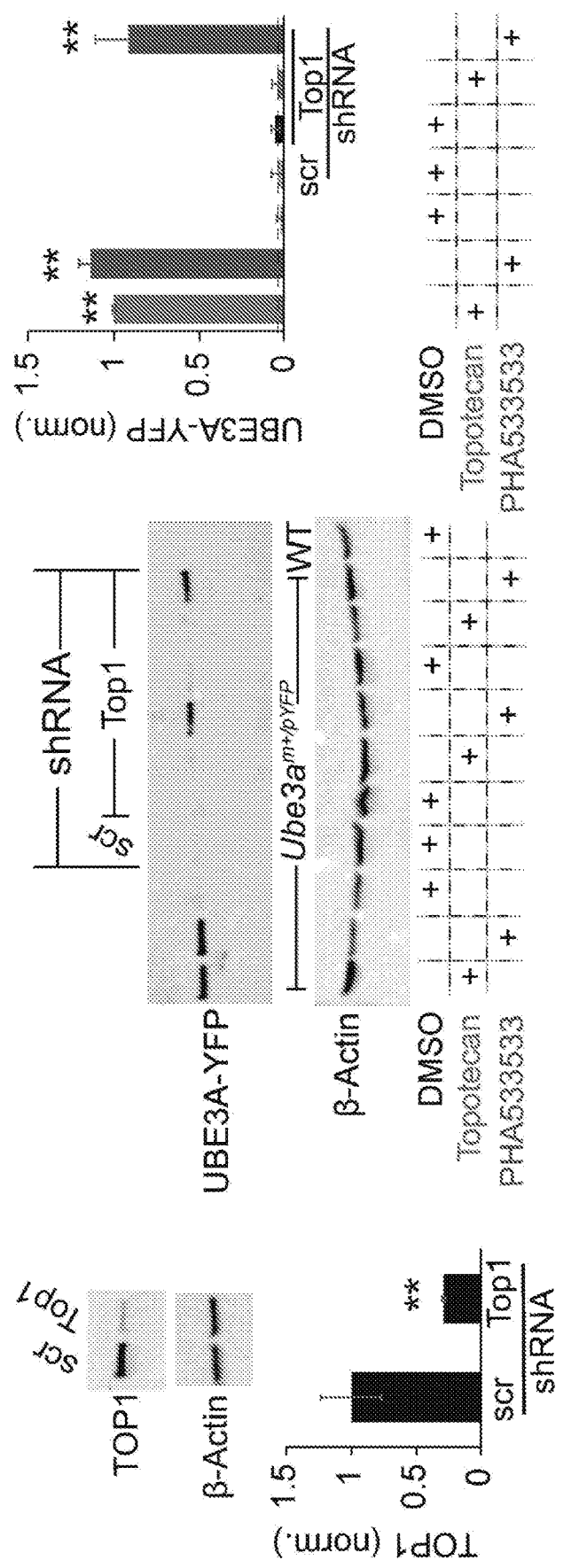

Downregulation of cyclin-dependent kinase 5 (CDK5) partially unsilences paternal Ube3a-YFP: Next, whether inhibiting potential molecular targets contributes to unsilencing paternal Ube3a was investigated. Since PHA533533 can inhibit CDK2 and CDK5, these kinases were individually knocked down by shRNA approaches to test whether direct targeting CDK2 or CDK5 is sufficient for unsilencing of paternal Ube3a. Thus, the initial hypothesis that CDK2 and CKD5 are common targets for the novel unsilencing compounds was tested. CDK2 knockdown did not unsilence paternal Ube3a-YFP by itself, nor did it occlude the pharmacological unsilencing of paternal Ube3a-YFP (FIG. 4A). In contrast, CDK5 knockdown partially unsilenced paternal Ube3a-YFP (FIG. 4B). These data suggest that off-target effects of PHA533533 may contribute to paternal Ube3a unsilencing. Next, whether the observed unsilencing effects might be mediated through off-target effects on Top1 was tested, because it had been previously shown that Top1 is a target of topotecan to unsilence paternal Ube3a. In addition, Top1 depletion occludes the ability of topotecan to unsilence paternal Ube3a, and a Top1 cleavage complex is required for unsilencing. It was first replicated that Top1 knockdown by itself did not unsilence paternal Ube3a-YFP and that it could occlude unsilencing by topotecan (FIG. 4C). In contrast, PHA533533 still unsilenced paternal Ube3a-YFP when Top1 was knocked down, suggesting that Top1 is not the target for PHA533533 or Compound X and further distinguishing the mechanism of action of these compounds from Top1 inhibitors such as topotecan.

Figure 5A:
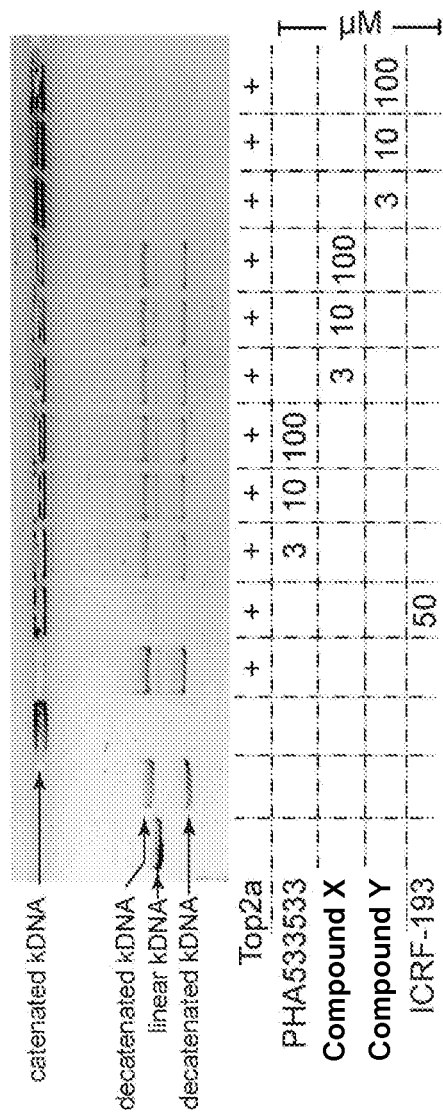
FIGS. 5A-5F show dual inhibition of CDK5 and DOT1L may be required to unsilence paternal Ube3a-YFP.

Inhibition of both cyclin-dependent kinase 5 (CDK5) and disruptor of telomeric silencing 1-like (DOT1L: histone H3 lysine 79 specific methyltransferase), unsilences paternal Ube3a-YFP in vitro: It was further explored whether PHA533533 and Compound X might act as topoisomerase inhibitors such as indenoisoquinoline- or camptothecin-derived topoisomerase inhibitors. Accordingly, topoisomerase-based DNA relaxation assays were performed to test whether the compounds inhibit topoisomerases. In the presence of Top2a, kinetoplast DNA (kDNA) was unwound and migrated further into the agarose gel (decatenated kDNA), while treatment with ICRF-193, a known Top2a and 2b inhibitor, inhibits the relaxation of catenated kDNA, which remains at the top of the agarose gel. PHA533533 and Compound X partially inhibited Top2a because both catenated and decatenated kDNA were observed. Control Compound Y inhibited Top2a, in a manner that appears comparable to ICRF-193 (FIG. 5A). However, these compounds did not inhibit either Top1 (FIG. 7A) or Top2b (FIG. 7B) as measured in DNA relaxation assays. Thus, the data largely exclude the possibility that the novel Ube3a unsilencing compounds act by inhibiting topoisomerases, suggesting that they instead employ novel mechanisms.

Figure 5B:
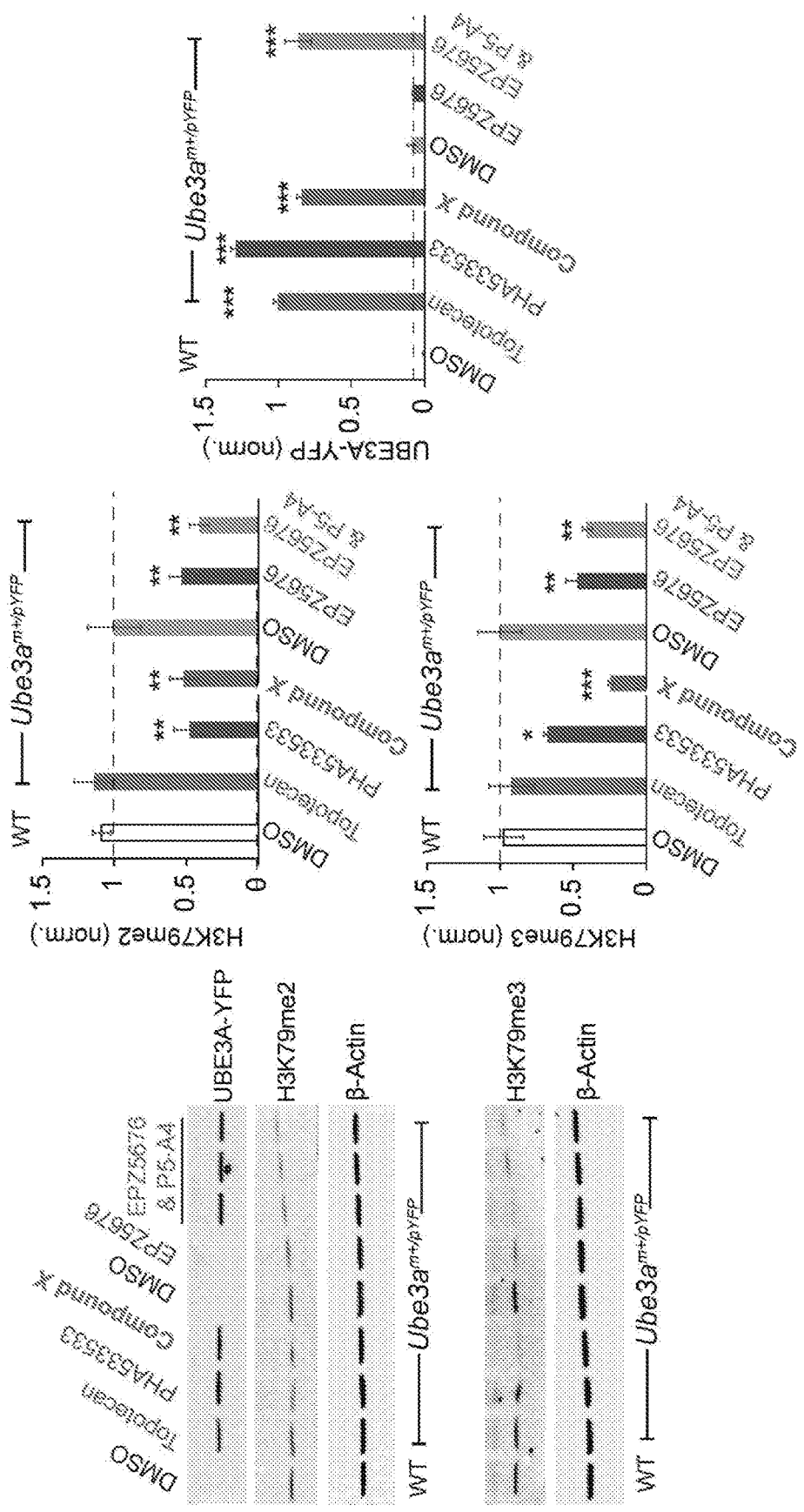
Figure 5C:
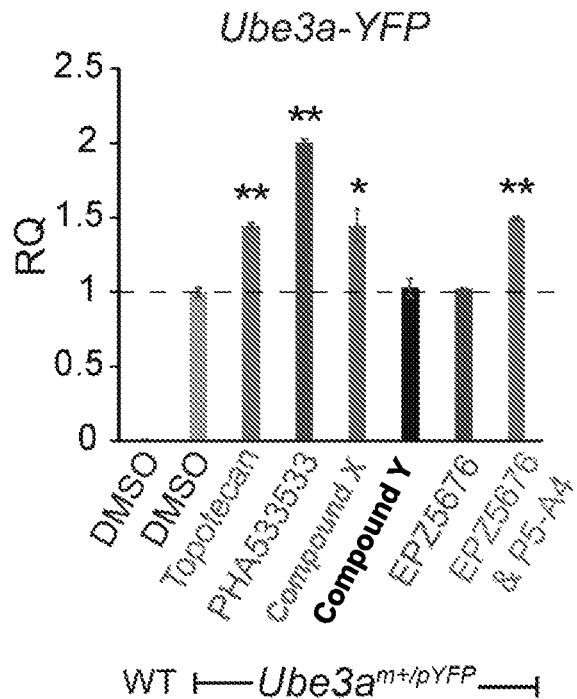
Figure 5D:
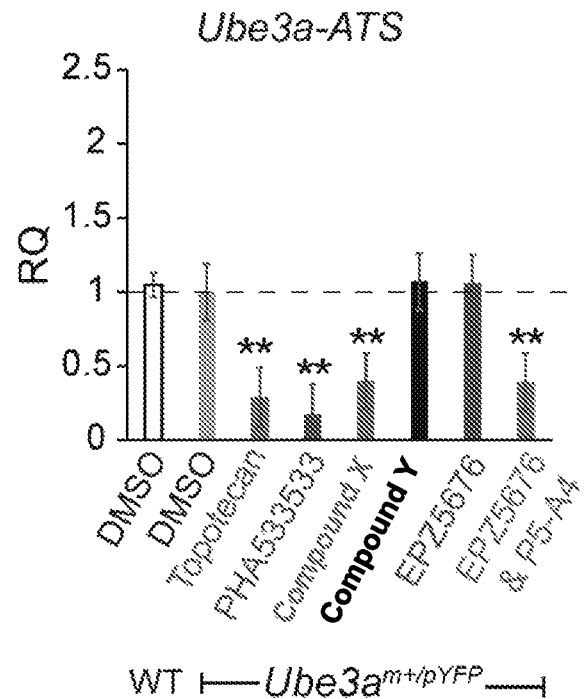
Figure 5E:
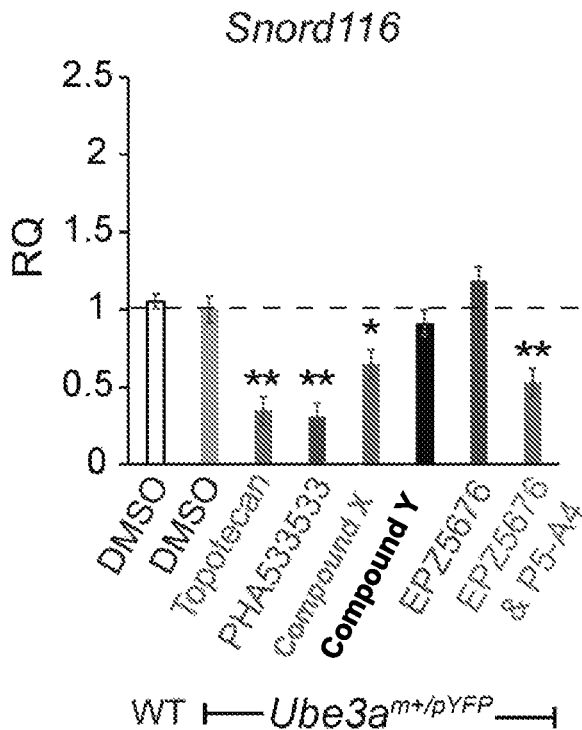
Figure 5F:
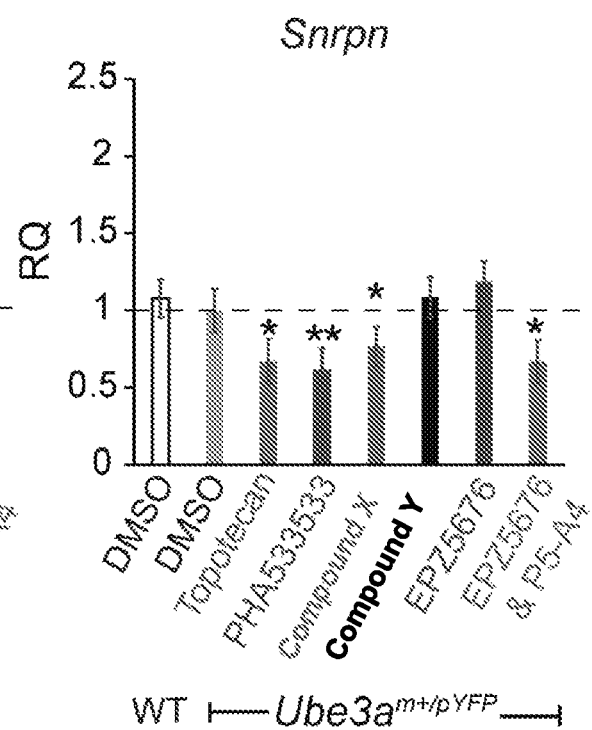
Figure 6:
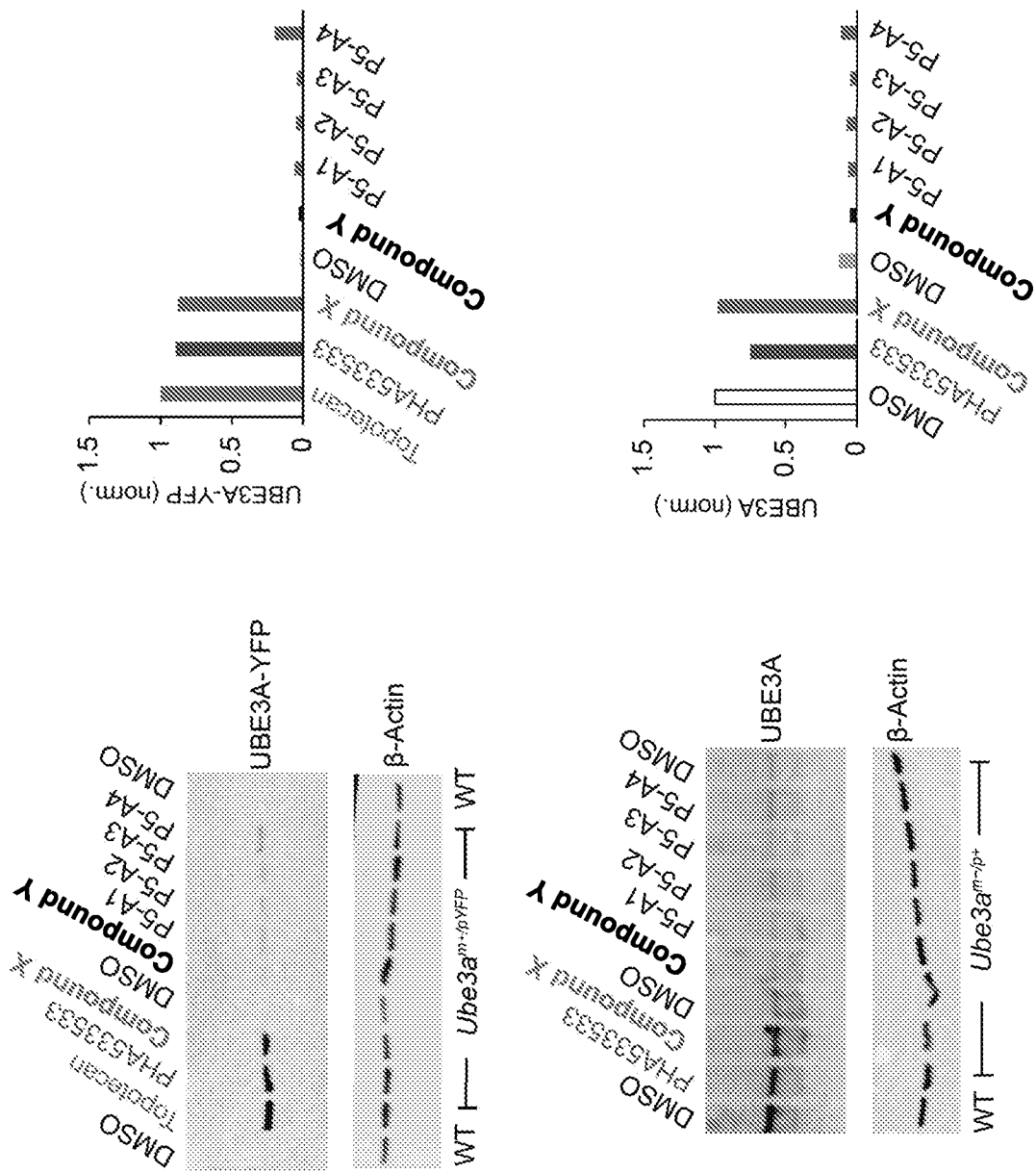
FIG. 6 shows four structural analogues of PHA533533 produced only modest paternal Ube3a unsilencing by western blot analysis.

The putative molecular target (i.e., DOT1L) of PHA533533 and Compound X prompted testing into whether paternal Ube3a could be unsilenced by inhibiting DOT1L solely or in combination with other targets such as CDK5. To this end, EPZ5676 was tested as a highly selective inhibitor of DOT1L (Daigle et al. Blood 2013; 122(6): 1017-1025). In addition, P5-A4 (FIG. 6); was tested as an analogue of PHA533533 that retains known inhibitory activity toward CDK2 and CDK5 but that is not predicted by DockoMatic to target DOT1L. As shown in FIG. 5B, dual treatment of EPZ5676 and P5-A4 unsilenced paternal Ube3a-YFP, whereas either EPZ5676 alone (FIG. 5B) or P5-A4 alone (FIG. 6) did not appreciably unsilence paternal Ube3a-YFP. In addition to EPZ5676 (positive control), PHA533533 and Compound X reduced methylation level on histone H3 lysine 79 (H3K79) (FIG. 5B), suggesting that PHA533533 and Compound X can inhibit DOT1L in agreement with our molecular prediction. Moreover, mRNAs of target genes were changed by the same treatment (FIGS. 5C-5F). In corroboration with the western blot analysis, it was found that mRNA of Ube3a-YFP was increased by combined treatment of EPZ5676 and P5-A4 (FIG. 5C). This dual pharmacological approach appeared to act by downregulating the Ube3a-ATS and its upstream genes Snord116 and Snrpn (FIGS. 5D-5F). These data indicate that PHA533533 and Compound X may share molecular targets, CDK5 and DOT1L, that act in concert to unsilence paternal Ube3a. As such, these compounds and their molecular targets may provide AS therapeutic avenues.

A high-content screen revealed two novel compounds, PHA533533 and Compound X, that can effectively unsilence the paternal Ube3a allele in mouse primary cortical neurons. These compounds do not appear to be acting through off-target effects on topoisomerases (i.e., Top1, Top2a, or Top2b), suggesting they have a novel mechanism of action distinct from previously identified small molecule Ube3a unsilencing agents. Instead, these compounds appear to be acting through a mechanism that jointly targets CDK5 and DOT1L.

Pharmacological properties of the novel unsilencers in vitro: The pharmacological profiles (potency, efficacy, and $LC_{50}$) of the two novel compounds can provide insights into whether they could be drug-like small molecules with clinical potential and how their pharmacological properties compare to another unsilencing agent, topotecan. PHA533533 has a slightly lower potency than topotecan, but has similar efficacy and cytotoxicity (FIG. 2). In contrast, Compound X showed comparable potency and efficacy to topotecan, but had slightly increased cytotoxicity than topotecan (FIG. 2). Even if PHA533533 and Compound X are not themselves viable options for treating AS, their chemical structures serve as a starting point for chemical modifications to improve potency, efficacy, and pharmacokinetic parameters.

Known and predicted molecular targets: This study sought to gain insights into the mechanism(s) driving paternal Ube3a unsilencing by understanding the known and predicted molecular targets of PHA533533 and Compound X. While PHA533533 has well established targets, CDK2 and CDK5, the molecular targets of Compound X are poorly understood. While not wishing to be bound to theory, we hypothesized that PHA533533 and Compound X may be acting, at least in part, through a previously undescribed mechanism. To address this hypothesis, DockoMatic was used to predict potential shared targets of the three compounds [the two active compounds, PHA533533 and Compound X, as well as the inactive compound, control Compound Y]. The modeling suggested that these compounds share CDK2, CDK5, and Top2a as potential targets. In addition, there is a shared, but unique target, DOT1L, between PHA533533 and Compound X, but not control Compound Y.

For the shared known and predicted targets (CDK2, CDK5, and Top2a), we can exclude the possibility of unsilencing through Top2a inhibition by our compounds because control Compound Y did not unsilence paternal Ube3a (FIG. 3). Four structural analogues of PHA533533 produced only modest paternal Ube3a unsilencing (FIG. 7), suggesting that inhibition of CDK2 or CDK5 by itself is unlikely to produce strong unsilencing. Consistent with this idea, shRNA-mediated knockdown of CDK2 failed to produce any observable unsilencing, while knockdown of CDK5 produced only partial unsilencing of paternal Ube3a-YFP (FIG. 4). These data suggest that PHA533533 and Compound X may act in concert through CDK5 inhibition and another mechanism, such as DOT1L inhibition. To further narrow the focus on DOT1L as a possible contributor to paternal Ube3a unsilencing, it was experimentally verified that PHA533533 and Compound X function as inhibitors of DOT1L (FIG. 5B), because DOT1L is the only methyltransferase catalyzing H3K79. Moreover, combined treatment to inhibit CDK5 (by P5-A4) and DOT1L (by EPZ5676) unsilenced paternal Ube3a-YFP (FIG. 5B). Therefore, the results of this study suggest that PHA533533 and Compound X may act in concert through CDK5 and DOT1L inhibition.

Potential mechanism of unsilencing paternal UBE3A: One potential unsilencing mechanism of our novel compounds is that they interfere with long gene transcription, as these compounds downregulated Ube3a-ATS, an extremely long transcript. However, there is no evidence proving that CDK5 is directly or indirectly involved in regulating RNA polymerase II (RNAPII) activity to our knowledge. On the other hand, DOT1L is known to be a direct interactor of RNAPII, which is responsible for the transcriptional elongation process and exon definition. Thus, inhibiting DOT1L activity may perturb the elongation process of actively transcribed genes such as Ube3a-ATS, supported by reports showing that the interaction of DOT1L with phosphor-Ser2 and/or Ser5 of the c-terminal domain (CTD) in RNAPII facilitates recruitment of DOT1L to actively-transcribed genes. However, data from this study indicate that DOT1L inhibition alone was not sufficient for unsilencing paternal Ube3a-YFP. Taken together with the results showing little to no unsilencing by CDK5 perturbation alone (i.e., using shRNA knockdown or using P5-A4), molecular interactions between CDK5 and DOT1L may mediate unsilencing of paternal Ube3a. Additional investigations are required to determine whether 1) changes in RNAPII activity are correlated with drug-mediated CDK5 and DOT1L inhibition, 2) the enrichment levels of histone modifications are correlated with transcriptional activity, 3) molecular interactions between CDK5 and DOT1L are associated with RNAPII activity and genomic imprinting, and/or 4) H3K79 methylation globally impacts chromatin structure in relation to transcription.

Developing AS therapeutics is an unmet need for patients and their families. This study identified PHA533533 and Compound X as novel Ube3a unsilencers that may act through their dual inhibition of CDK5 and DOT1L, as selective inhibition of either CDK5 or DOT1L alone through molecular or pharmacological blockade is not sufficient to effectively unsilence paternal Ube3a. While not wishing to be bound to theory, it is contemplated that the joint inhibition of CDK5 and DOT1L promotes paternal Ube3a unsilencing. This mechanism jointly targeting CDK5 and DOT1L could limit transcriptional elongation, or perhaps more specifically downregulate Ube3a-ATS, and as a result unsilence paternal Ube3a. This suggests that interference of UBE3A-ATS can be achieved by a manner distinct from topoisomerase inhibition. Therefore, the results reported herein provide a novel avenue to develop AS therapies using different classes of small molecules that should be advanced for preclinical testing of safety and CNS efficacy in mouse models of AS.

Example 2

Figure 8A:
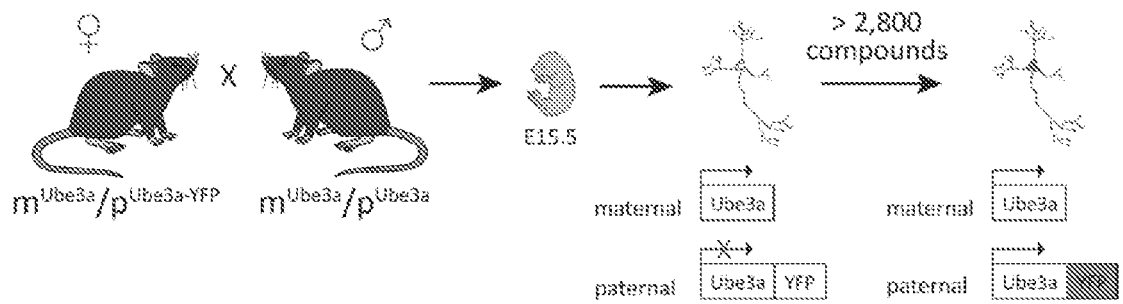
FIGS. 8A-8C show PHA533533 unsilencing of paternal Ube3a-YFP.
Figure 8B:
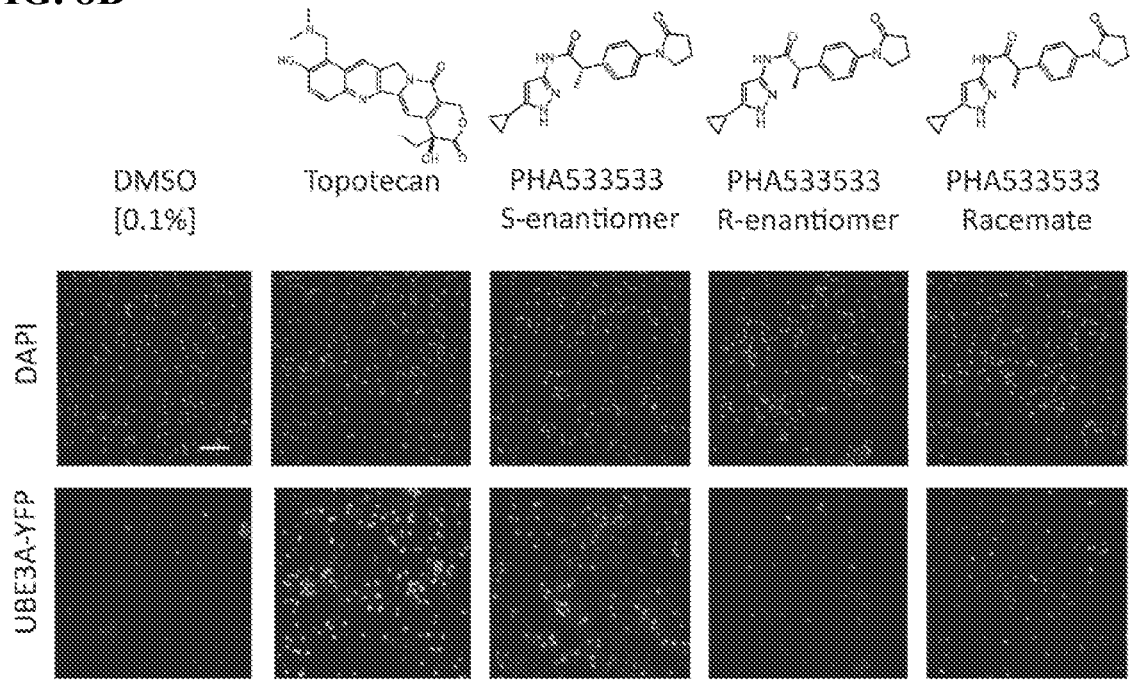
Figure 8C:
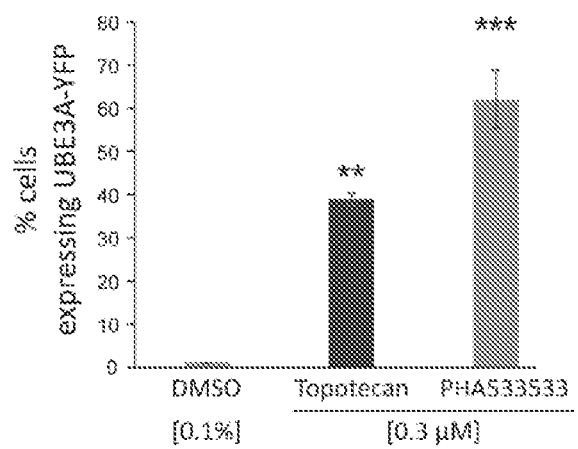

FIGS. 8A-8C show that PHA533533 produces unsilencing of paternal Ube3a-YFP. Small molecules were tested for their ability to unsilence paternal Ube3a in cultured cortical neurons derived from 15.5-day old embryos (E15.5) with a paternally inherited Ube3a-YFP allele. Paternal UBE3A-YFP levels were assessed using GFP antibody-enhanced fluorescence and high-content imaging. FIG. 8B shows DAPI (nuclear stain) and paternal UBE3A-YFP immunocytochemistry in cultured neurons treated with 0.1% DMSO (negative control), topotecan (positive control), S-enantiomer of PHA533533, R-enantiomer of PHA533533, or a racemic mixture of S and R enantiomers of PHA533533. FIG. 8C shows quantitative analysis of the percentage of cells expressing paternal UBE3A-YFP, calculated by dividing the number of YFP-positive cells by the total number of DAPI-positive nuclei. These data indicate that PHA533533 can unsilence paternal Ube3a-YFP.

The pharmacological profile of PHA533533 in unsilencing paternal Ube3a-YFP in vitro was also examined. FIG. 9A shows dose-dependence of PHA533533 compared to topotecan in unsilencing paternal Ube3a-YFP. FIG. 9B shows dose-dependent cytotoxicity of PHA533533 compared to topotecan. $EC_{50}$ (FIG. 9C), $E_{max}$ (FIG. 9D), and $LC_{50}$ (FIG. 9E) of the compounds were also determined.

Similar studies were performed using PHA533533 analogs. Dose-dependence of unsilencing paternal Ube3a-YFP by PHA533533 analogs (FIG. 10A) PNU0292137, (FIG. 10B) PNU0278497, and (FIG. 10C) PHA00543738 were determined. FIG. 10D shows $EC_{50}$ and FIG. 10E shows $E_{max}$ of the PHA533533 analogs compared to PHA533533. These data show that these compounds could not produce appreciable increases in paternal UBE3A-YFP or paternal UBE3A. Therefore, the unsilencing of paternal UBE3A was specific to PHA533533.

Figure 11A:
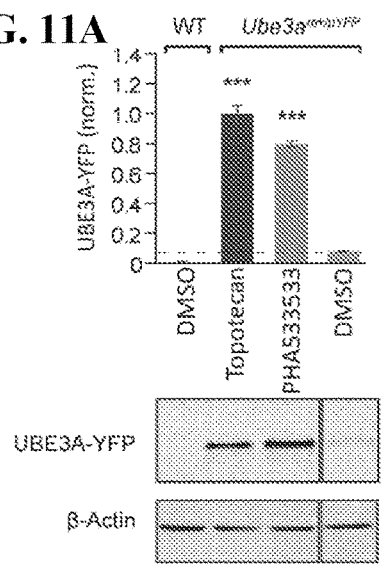
FIGS. 11A-11B show that PHA533533 treatment produces UBE3A protein from the paternal allele. Western blot analyses show UBE3A-YFP (FIG. 11A) and UBE3A (FIG. 11B) protein from the paternal allele. Whole cell lysates from cultured mouse cortical neurons (wildtype, Ube3a$^{m+/pYFP}$ or Ube3a$^{m-/p+}$ as indicated) were resolved using SDS-PAGE and immunoblotted with anti-GFP (FIG. 11A), anti-Ube3a (FIG. 11B), or anti-β-actin (FIGS. 11A-11B) antibodies. Graphs show quantification of normalized signal. DMSO=0.1% vehicle control; Topotecan=0.3 µM; PHA533533=1.0 µM (n=3/group, *p<0.05, p<0.01, *p<0.001).
Figure 11B:
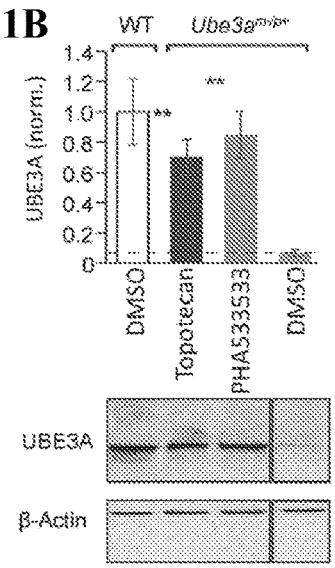
Figure 12A:
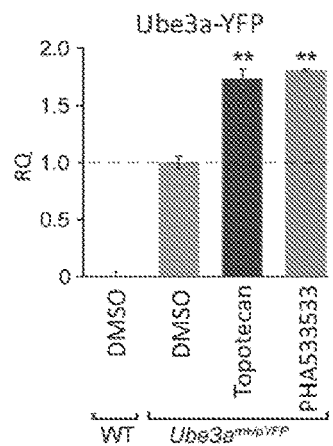
FIGS. 12A-12D show PHA533533 treatment downregulates Ube3a-ATS in neurons. Quantitative RT-PCR (qPCR) changes in mRNA of paternal Ube3a-YFP (FIG. 12A), Ube3a-antisense (ATS) (FIG. 12B), Snord116 (FIG. 12C), and Snrpn (FIG. 12D) in cultured mouse cortical neurons (wildtype or Ube3a$^{m+/pYFP}$ as indicated) after drug treatment are shown. Graphs represent relative mRNA levels normalized to β-actin and shown as mean s.e.m. DMSO=0.1% vehicle control; Topotecan=0.3 µM; PHA533533=1.0 µM (RQ: Relative quantity, n=3/group, *p<0.05, p<0.01, *p<0.001).
Figure 12B:
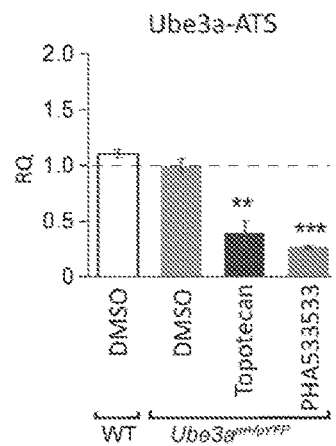
Figure 12C:
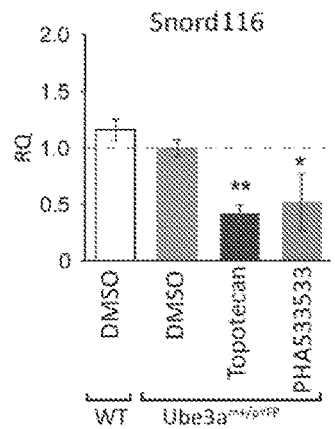
Figure 12D:
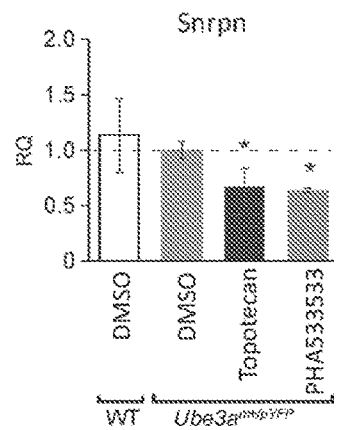

FIGS. 11A-11B show that PHA533533 treatment produces UBE3A protein from the paternal allele. Western blot analyses show that, like topotecan, PHA533533 can produce UBE3A-YFP (FIG. 11A) and UBE3A (FIG. 11B) protein from the paternal allele.

FIGS. 12A-12D show PHA533533 treatment downregulates Ube3a-ATS in neurons. Quantitative RT-PCR (qPCR) revealed changes in mRNA of paternal Ube3a-YFP (FIG. 12A), Ube3a-antisense (ATS) (FIG. 12B), Snord116 (FIG. 12C), and Snrpn (FIG. 12D) in cultured mouse cortical neurons (wildtype or $Ube3a^{m+/pYFP}$ as indicated) after drug treatment.

Figure 13G:
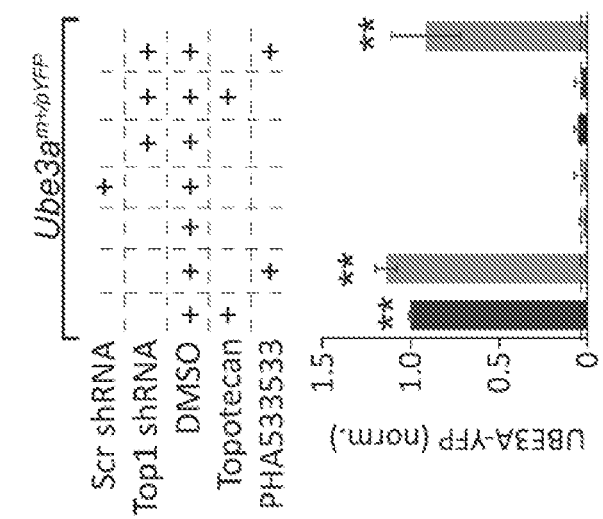
Figure 13H:
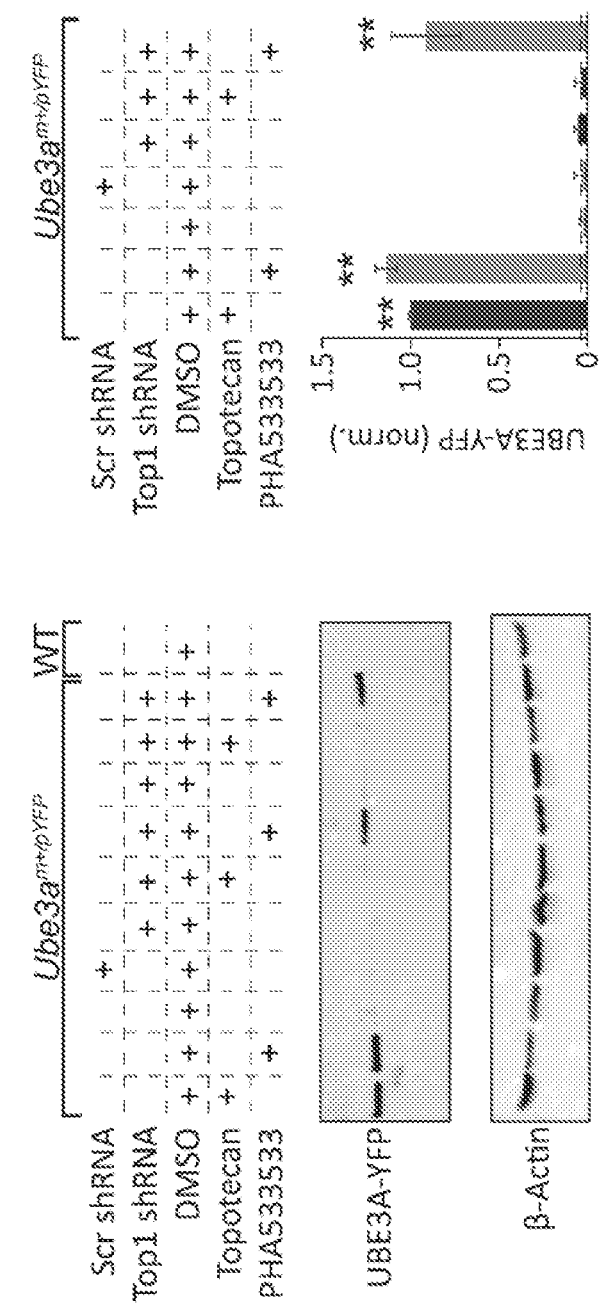
Figure 13I:
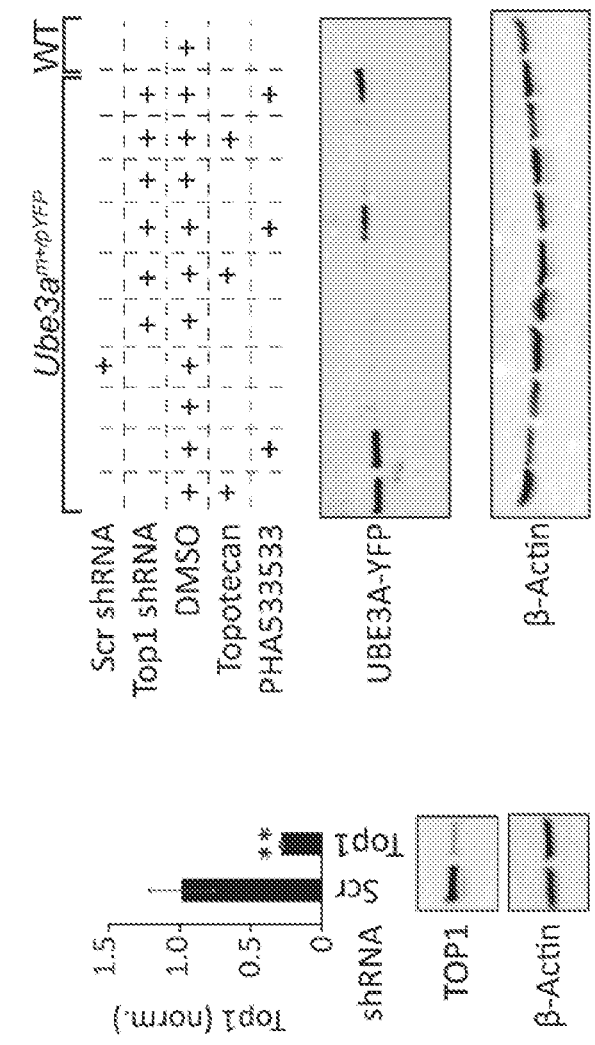

FIGS. 13A-13I show that selective knockdown of established PHA533533 molecular targets is not sufficient to unsilence paternal Ube3a-YFP as effectively as PHA533533. FIG. 13A shows efficient knockdown of cyclin-dependent kinase 2 (CDK2) using shRNA approach. FIG. 13B shows Western blot analysis and FIG. 13C shows quantification that shRNA knockdown does not unsilence paternal Ube3a-YFP unless neurons were treated with topotecan or PHA533533. FIG. 13D shows efficient knockdown of cyclin-dependent kinase 5 (CDK5) by shRNA. FIG. 13E shows Western blot analysis and FIG. 13F shows quantification that CDK5 knockdown can partially unsilence paternal Ube3a-YFP, and this unsilencing was further enhanced by treatment with topotecan or PHA533533. FIG. 13G show shRNA knockdown of topoisomerase 1 (Top1). FIG. 13H shows Western blot analysis and FIG. 13I shows quantification that knockdown of Top1 did not unsilence paternal Ube3a-YFP, but Top1 knockdown occluded the ability of topotecan, but not PHA533533, to unsilence paternal Ube3a-YFP.

Fluorescence immunocytochemistry and high content imaging analysis: After 72-hour drug treatment, the neurons were fixed with 4% paraformaldehyde in phosphate-buffered saline (PBS) at room temperature for 10 min. After brief washing with PBS three times, neurons were permeabilized with 1% Triton-X 100 in PBS at room temperature for 10 min, followed by blocking with 5% normal goat serum in 0.1% Triton-X 100 in 1×PBS at room temperature. 30 min after blocking, neurons were incubated with primary antibodies rabbit anti-GFP (1:1000, NB 600308, Novus Biologicals) and mouse anti-NeuN (1:500, MAB 377, Millipore) at 4° C. overnight. Neurons were then briefly washed with 1×PBS followed by incubation with secondary antibodies goat anti-rabbit Alexa Fluor 488 (1:500, A11008, Thermo Fisher/Invitrogen) and anti-mouse Alexa Fluor 568 (1:500, A21124, ThermoFisher/Invitrogen) together with DAPI (4',6-diamidino-2-phenylindole) at room temperature for 60 min. Following secondary antibody incubation, neurons were washed with 1×PBS and fluorescent images were acquired using Nikon Ti2 eclipse fluorescent microscope (Nikon Instruments Inc., Melville, NY, USA). Antibody-enhanced UBE3A-YFP fluorescence intensities were determined from DAPI and NeuN double-positive individual neurons in drug-treated wells and normalized to neurons in untreated wells. All acquired images were analyzed by Nikon NIS-Elements software (Nikon Instruments Inc., Melville, NY, USA). Sigmoidal curve fitting for the dose response analysis was performed using GraphPad Prism software version 8.0 (GraphPad Software, La Jolla, CA, USA). The calculated $EC_{50}$ values (potencies) and Y value top plateau (estimated efficacies) enables comparative analyses of the relative potency and efficacy of the identified compounds.

Example 3

Figure 14A:
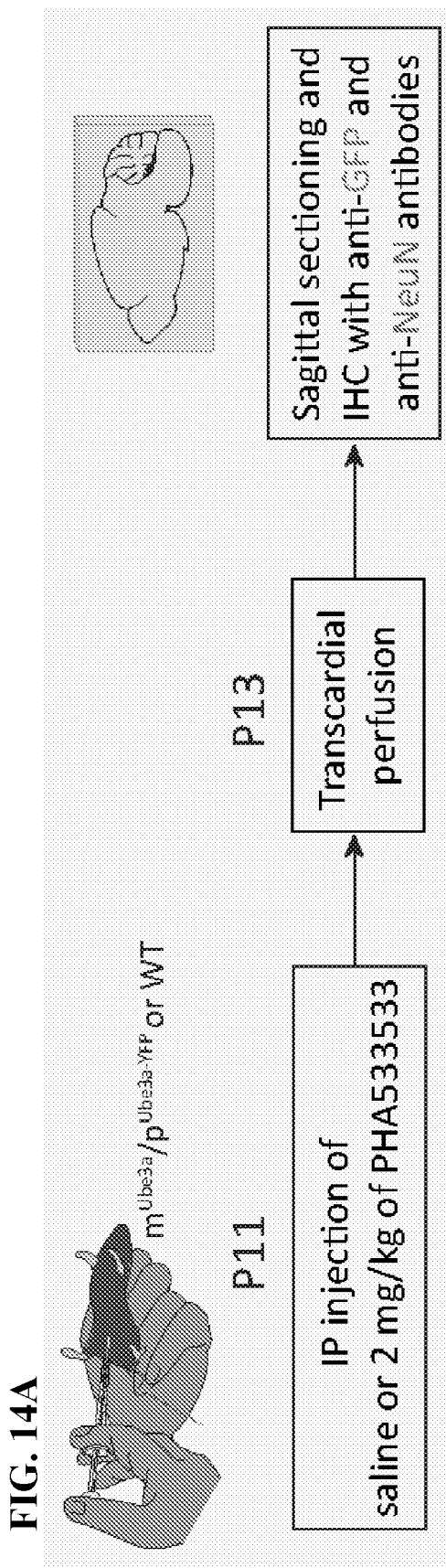

The aim of these experiments was to determine if PHA533533 could unsilence the paternal Ube3a allele in vivo. To this end, PHA533533 (2 mg/kg body weight) or saline vehicle control was administered into $Ube3a^{m+/pYFP}$ mice by intraperitoneal injection (IP) at postnatal day 11 (P11) and the mice were sacrificed two days after drug administration at P13 (FIG. 14A). Saline treated wild type and $Ube3a^{m+/pYFP}$ mice served as immunohistochemistry controls showing the absence of GFP-immunoreactivity in wild type mice (FIG. 14B) and expected paternal UBE3A-YFP protein expression in glial cells and in newly generated immature neurons in $Ube3a^{m+/pYFP}$ mice (FIG. 14C; Judson et al. J Comp Neurol 2014 522(8):1874-96), respectively. Peripheral delivery (i.p.) of PHA533533 successfully upregulated paternal Ube3a-YFP throughout the brain (FIG. 14D). Examining the hippocampal CA3 region more closely, costaining of GFP and the neuronal marker NeuN showed near-complete co-localization (FIG. 14E), indicating efficient unsilencing of paternal Ube3a-YFP in mature neurons. These data indicate that PHA533533 successfully unsilences the paternal Ube3a allele throughout the nervous system.

Intraperitoneal injection and immunohistochemistry: PHA533533 (2 mg/kg body weight) or saline vehicle (0.9% NaCl) was injected intraperitoneally (IP) into unanesthetized postnatal day 11 (P11) mice using 27-gauge needle attached to a 1 ml syringe. PHA533533 was dissolved with 7.5% DMSO in saline. P13 mice were deeply anesthetized with euthasol (100 mg/kg, i.p.) prior to transcardial perfusion with phosphate-buffered saline (PBS), pH 7.4, followed by phosphate-buffered 4% paraformaldehyde, pH 7.4. Perfused brains were postfixed overnight and cryoprotected with 30% sucrose in PBS, pH 7.4, for two days. Cryoprotected brains were frozen on dry ice and cut into 40 μm-thick sections with a sliding microtome (Thermo Scientific, Kalamazoo, MI, USA). Sections were stored in a cryopreservative solution (by volume: 45% PBS, 30% ethylene glycol, 25% glycerol) at −20° C. until they were processed for free-floating immunohistochemistry (IHC). For IHC, sections were rinsed several times in PBS before blocking in PBS plus 5% normal goat serum and 0.2% Triton-X-100 (NGST) for 1 hour at room temperature. Sections were incubated with rabbit anti-GFP (1:1000, NB 600308, Novus Biologicals) and mouse anti-NeuN (1:500, MAB 377, Millipore) primary antibodies diluted in NGST for 48 hours at 4° C. Sections were then washed several times in PBS containing 0.2% Triton-X-100 (PBST) before incubation with goat anti-rabbit Alexa Fluor 488 (1:500, A11008, Thermo Fisher/Invitrogen) and anti-mouse Alexa Fluor 568 (1:500, A21124, ThermoFisher/Invitrogen) secondary antibodies together with DAPI (4',6-diamidino-2-phenylindole) all diluted in NGST for 1 hour at room temperature. Brain sections compared within figure were stained within the same experiment, under identical conditions. Images were acquired using a Zeiss LSM 710 confocal microscope (Carl Zeiss Inc.).

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A method of treating Angelman Syndrome in a human subject, comprising administering to the subject an effective amount of PHA533533 or a salt thereof, (R)-N-(5-cyclopropyl-1H-pyrazol-3-yl)-2-(4-(2-oxopyrrolidin-1-yl)phenyl) propenamide, (S)-N-(5-cyclopropyl-1H-pyrazol-3-yl)-2-(4-(2-oxooxazolidin-3-yl)phenyl) propenamide, and/or EPZ5676 in any combination, thereby treating Angelman syndrome in the subject.

2. The method of claim 1, wherein the effective amount of PHA533533 or a salt thereof, (R)-N-(5-cyclopropyl-1H-pyrazol-3-yl)-2-(4-(2-oxopyrrolidin-1-yl)phenyl) propenamide, (S)-N-(5-cyclopropyl-1H-pyrazol-3-yl)-2-(4-(2-oxooxazolidin-3-yl)phenyl) propenamide, and/or EPZ5676 in any combination inhibits a target selected from the group consisting of CDK5, CDK2, DOT1L, ATXR5, CBP, CDK6, CDK8, CDK9, CDK16, CDKL3, EHMT1, EHMT2, KMT5C, SETD7, SMYD1, SMYD3, and any combination thereof.

3. The method of claim 1, wherein the effective amount of PHA533533 or a salt thereof, (R)-N-(5-cyclopropyl-1H-pyrazol-3-yl)-2-(4-(2-oxopyrrolidin-1-yl)phenyl) propenamide, (S)-N-(5-cyclopropyl-1H-pyrazol-3-yl)-2-(4-(2-oxooxazolidin-3-yl)phenyl) propenamide, and/or EPZ5676 in any combination has an efficiency Emax of at least 1.25 fold over control.

4. The method of claim 1, wherein the effective amount of PHA533533 or a salt thereof, (R)-N-(5-cyclopropyl-1H-pyrazol-3-yl)-2-(4-(2-oxopyrrolidin-1-yl)phenyl) propenamide, (S)-N-(5-cyclopropyl-1H-pyrazol-3-yl)-2-(4-(2-oxooxazolidin-3-yl)phenyl) propenamide, and/or EPZ5676 in any combination has an efficiency Emax of at least 2.5 fold over control.

5. The method of claim 1, comprising an effective amount of PHA533533 or a salt thereof.

* * * * *

UNITED STATES PATENT AND TRADEMARK OFFICE
CERTIFICATE OF CORRECTION

PATENT NO. : 12,310,947 B2
APPLICATION NO. : 17/625604
DATED : May 27, 2025
INVENTOR(S) : Philpot et al.

Page 1 of 1

It is certified that error appears in the above-identified patent and that said Letters Patent is hereby corrected as shown below:

In the Specification

Column 4, Line 56: Please correct "mean s.e.m." to read --mean±s.e.m.--

Column 5, Line 18: Please correct "mean s.e.m." to read --mean±s.e.m.--

Column 14, Line 35: Please correct "(Ube3a$^{m-/P+}$) To" to read --(Ube3a$^{m-/p+}$): To--

Column 14, Line 57: Please correct "(Ube3a$^{m+/p+}$) This" to read --(Ube3a$^{m-/p+}$). This--

In the Claims

Column 23, Line 48, Claim 2: Please correct "DOTIL" to read --DOT1L--

Signed and Sealed this
Sixteenth Day of September, 2025

Coke Morgan Stewart
*Acting Director of the United States Patent and Trademark Office*